(12) United States Patent
Primor

(10) Patent No.: US 11,419,913 B2
(45) Date of Patent: Aug. 23, 2022

(54) PHARMACEUTICAL COMPOSITIONS FOR INHIBITING INFLAMMATORY CYTOKINES

(71) Applicant: S.I.S. SHULOV INNOVATIVE SCIENCE LTD., Rehovot (IL)

(72) Inventor: Naftali Primor, Jerusalem (IL)

(73) Assignee: S.I.S SHULOV INNOVATIVE SCIENCE LTD., Rehovot (IL)

( * ) Notice: Subject to any disclaimer, the term of this patent is extended or adjusted under 35 U.S.C. 154(b) by 0 days.

(21) Appl. No.: 17/041,051

(22) PCT Filed: Mar. 28, 2019

(86) PCT No.: PCT/IL2019/050359
§ 371 (c)(1),
(2) Date: Sep. 24, 2020

(87) PCT Pub. No.: WO2019/186561
PCT Pub. Date: Oct. 3, 2019

(65) Prior Publication Data
US 2021/0138023 A1    May 13, 2021

Related U.S. Application Data

(60) Provisional application No. 62/649,940, filed on Mar. 29, 2018.

(51) Int. Cl.
| | | |
|---|---|---|
| *A61K 38/07* | (2006.01) | |
| *A61P 27/02* | (2006.01) | |
| *A61P 37/02* | (2006.01) | |
| *A61P 17/00* | (2006.01) | |
| *A61P 19/02* | (2006.01) | |
| *A61P 29/00* | (2006.01) | |

(52) U.S. Cl.
CPC .............. *A61K 38/07* (2013.01); *A61P 17/00* (2018.01); *A61P 19/02* (2018.01); *A61P 27/02* (2018.01); *A61P 29/00* (2018.01); *A61P 37/02* (2018.01)

(58) Field of Classification Search
CPC .......... A61P 17/00; A61P 29/00; A61P 27/02; A61P 37/02; A61P 19/02; A61K 38/07
See application file for complete search history.

(56) References Cited

U.S. PATENT DOCUMENTS

| | | | |
|---|---|---|---|
| 4,619,916 A | 10/1986 | Di Stazio | |
| 6,525,030 B1 | 2/2003 | Eriksson | |
| 7,220,725 B2 | 5/2007 | Shulov | |
| 9,012,397 B2 | 4/2015 | Primor | |
| 2013/0310309 A1* | 11/2013 | Primor | A61P 17/02 514/4.2 |

FOREIGN PATENT DOCUMENTS

| | | |
|---|---|---|
| WO | 0212269 A2 | 2/2002 |
| WO | 2012131676 A1 | 10/2012 |

OTHER PUBLICATIONS

Avci et al., (2013) Animal models of skin disease for drug discovery. Expert Opin Drug Discov. Author manuscript; available in PMC Mar. 1, 2014. Published in final edited form as: Expert Opin Drug Discov 8(3): 331-355; 42 pages.

Barabino et al., (2005) The controlled-environment chamber: a new mouse model of dry eye. Invest Ophthalmol Vis Sci 46(8): 2766-2771.

Dartt et al., (1996) Vasoactive Intestinal Peptide-Stimulated Glycoconjugate Secretion from Conjunctival Goblet Cells. Experimental Eye Research 63(1): 27-33.

De Vos et al., (1995) Systemic anti-tumor necrosis factor antibody treatment exacerbates endotoxin-induced uveitis in the rat. Exp Eye Res 61(6): 667-675.

Ewald et al., (2017) Major differences between human atopic dermatitis and murine models, as determined by using global transcriptomic profiling. J Allergy Clin Immunol 139(2): 562-571.

Fingl E and Woodbury DM; Chapter 1: General Principles. In: The Pharmacological Basis of Therapeutics, fifth edition. Edited by Louis S. Goodman and Alfred Gilman. Macmillan, 866 Third Ave., New York, NY 10022, 1975. 46 pages.

Galli et al., (2016) Mast cells and IgE in defense against venoms: Possible "good side" of allergy? Allergol Int 65(1): 3-15.

Gaynes et al., (2013) Efficacy of a novel synthetic topical tetrapeptide on eliciting analgesia subsequent to experimentally induced chemical corneal injury. ARVO Annual Meeting Abstract. Investigative Ophthalmology & Visual Science 54(15): E-Abstract 5416.

Gilbard et al., (1978) Osmolarity of tear microvolumes in keratoconjunctivitis sicca. Arch Ophthalmol 96(4): 677-681.

Hessen and Akpek (2014) Dry eye: an inflammatory ocular disease. J Ophthalmic Vis Res 9(2): 240-250.

Jin et al., (2009) Animal models of atopic dermatitis. J Invest Dermatol 129(1): 31-40.

Kelly and Grayson (2016) Immunoglobulin E, what is it good for? Ann Allergy Asthma Immunol 116(3): 183-187.

Lee et al., (2012) The effect of adipose-derived stem cell-cultured media on oxazolone treated atopic dermatitis-like murine model. Ann Dermatol 24(2): 181-188.

Oettgen (2016) Fifty years later: Emerging functions of IgE antibodies in host defense, immune regulation, and allergic diseases. J Allergy Clin Immunol 137(6): 1631-1645.

Petersen (2006) In vivo pharmacological disease models for psoriasis and atopic dermatitis in drug discovery. Basic Clin Pharmacol Toxicol 99(2): 104-115.

Traidl et al., (1999) Inhibition of allergic contact dermatitis to DNCB but not to oxazolone in interleukin-4-deficient mice. J Invest Dermatol 112(4): 476-482.

(Continued)

*Primary Examiner* — Li N Komatsu
(74) *Attorney, Agent, or Firm* — J.A. Lindeman & Co., PLLC

(57) ABSTRACT

Pharmaceutical compositions comprising specific tetrapeptides, for use in reducing the release or inhibiting the activity of inflammatory cytokines and mediator and treatment of diseases and disorders associated with these cytokines and mediators.

15 Claims, 16 Drawing Sheets

Specification includes a Sequence Listing.

(56) References Cited

OTHER PUBLICATIONS

Caracas et al., (2009) The use of lidocaine as an anti-inflammatory substance: a systematic review. J Dent 37(2): 93-97.

Gambino Frank et al.,: "Anti-inflammatory action of a novel tetrapeptide in a corneal epithelial cell culture model", Apr. 29, 2018 (Apr. 29, 2018); retrieved from the internet: URL: https://iovs.arvojournals.org/article.aspx?articleid=2691598 [retrieved on Oct. 26, 2021]. 2 pages.

Guo et al., (2012) Prevention of LPS-induced acute lung injury in mice by progranulin. Mediators Inflamm 2012: 540794; 11 pages.

Mei et al., (2007) Prevention of LPS-induced acute lung injury in mice by mesenchymal stem cells overexpressing angiopoietin 1. PLoS Med 4(9): e269; 13 pages.

Ruan et al., (2013) Anti-inflammatory effects of Neurotoxin-Nna, a peptide separated from the venom of Naja naja atra. BMC Complement Altern Med 13: 86; 5 pages.

Zack Stephanie: "Lidocaine attenuates an induced inflammatory response". Aug. 1, 2018 (Aug. 1, 2018); retrieved from the internet: URL: https://ecommons.luc.edu/cgi/viewcontent.cgi?article=4713&context=luc_theses [retrieved on Oct. 26, 2021]. 101 pages.

\* cited by examiner

PHARMACEUTICAL COMPOSITIONS FOR INHIBITING INFLAMMATORY CYTOKINES

FIELD OF THE INVENTION

The present invention provides pharmaceutical compositions and methods for amelioration of symptoms associated with the release of inflammatory cytokines in inflammatory conditions including but not limited to inflammatory eye disorders.

BACKGROUND OF THE INVENTION

Inflammation is part of the complex biological response of body tissues to harmful stimuli, such as pathogens, damaged cells, or irritants, and is a protective response involving immune cells, blood vessels, and molecular mediators. The function of inflammation is to eliminate the initial cause of cell injury, clear out necrotic cells and tissues damaged from the original insult and the inflammatory process, and initiate tissue repair.

The classical signs of inflammation are heat, pain, redness, swelling, and loss of function. Inflammation is a generic response, and therefore it is considered as a mechanism of innate immunity.

Inflammatory diseases include a vast array of disorders and conditions that are characterized by inflammation. Examples include allergy, asthma, transplant rejection, autoimmune diseases, and ocular inflammation, to name just a few.

Inflammatory Eye Disorders

Uveitis is a general term describing a group of inflammatory eye diseases that can slightly reduce vision or lead to severe vision loss. The diseases often affect a part of the eye called the uvea but are not limited to this part of the eyes. These diseases also affect the lens, retina, optic nerve, and vitreous, producing reduced vision or blindness. Uveitis may be caused by problems or diseases occurring in the eye or it can be part of an inflammatory disease affecting other parts of the body. Uveitis can be acute or chronic and usually categorized as infectious or noninfectious.

Keratoconjunctivitis sicca, also known as dry eye disease (DED) or dry eye syndrome (DES), is a common ocular disease prompting millions of individuals to seek ophthalmological care. Regardless of the underlying etiology, dry eye has been shown to be associated with abnormalities in the pre-corneal tear film and subsequent inflammatory changes in the entire ocular surface including the adnexa, conjunctiva and cornea. Activation of inflammatory cytokines, for example, IL-6 play critical role in the pathophysiology of DED.

Since the recognition of the role of inflammation in dry eye, a number of treatments have been investigated designed to inhibit various inflammatory pathways, for example cyclosporine A, corticosteroids, tacrolimus, tetracycline derivatives and autologous serum (Michelle Hessen M., and Karamursel Akpek E J Ophthalmic Vis Res. 2014, 9(2), 240-250).

U.S. Pat. No. 4,619,916 teaches 13 tri-peptides of the formula pGlu-X-Trp, where pGlu is cyclized glutamic acid (pyroglutamic acid) and X may be Gly, Val, Glu, Asp, Ser, Ala, Asn, Gln, Ile, Leu, Pro, Lys and Arg. The reference does not describe or suggest a use of the peptides for treating inflammation.

U.S. Pat. No. 7,220,725 and International Patent Publication WO200212269 teach novel peptides including pGlu-Asn-Trp-Lys(Octanoyl)-OH (ZEP3, SEQ ID NO:1) and pGlu-Asn-Trp-Thr-OH (ZEP4, SEQ ID NO:2) and use thereof for treating pain. The reference does not describe or suggest a use of the peptides for treating inflammation.

U.S. Pat. No. 9,012,397 and WO2012/131676 teach topical pharmaceutical compositions including the peptides ZEP3 or ZEP4 and use thereof for ameliorating symptoms of skin disorders. The reference does not describe or suggest a use of the peptides for treating inflammation.

Gaynes et al. (Invest. Ophthalmol. Vis. Sci. 54, E-Abstract 5416, 2013) describe an analgesic effect of the peptide ZEP4 in reducing ocular pain and modifying pathways of nociception in a rat model of experimentally induced chemical corneal injury. The reference does not describe or suggest an anti-inflammatory activity of the peptide.

The present invention addresses the continued need to improve and develop new safe and effective treatments that ameliorate inflammatory conditions by intervening in the inflammatory cascade.

SUMMARY OF THE INVENTION

The present invention provides compositions and methods for the amelioration of symptoms associated with the release of inflammatory cytokines. These cytokines are known to be a part of the etiology and pathology of many inflammatory disorders. The diseases and disorders amenable to treatment with the compositions of the invention include but are not limited to inflammatory diseases of the eye, ear, lung, and bowel. The diseases and disorders amenable to treatment also include autoimmune diseases where the administration of the medicaments may be chronic administration in order to prevent exacerbations.

The present invention is based in part on the finding in in-vitro and in-vivo models, that the peptides denoted ZEP3 and ZEP4 show unexpectedly strong activity in attenuating the expression and/or release of inflammatory and pro-inflammatory mediators, including the specific cytokines interferon gamma (IFN-gamma, IFNγ), interleukin 1 beta (IL-1 beta, IL-1β), interleukin 10 (IL-10), tumor necrosis factor alpha (TNF alpha, TNFα), and interleukin 6 (IL-6), and the mediators reactive oxygen species (ROS) and RANTES (Regulated upon activation normal T cell expressed and presumably secreted).

It was surprisingly found that the activity of the peptides in inhibition of the inflammatory cascades, is exerted even when the peptides are administered before the inflammatory reaction is initiated. Thus, the peptides can ameliorate or suppress the symptoms induced in various inflammatory diseases and disorders and can be useful to eliminate the inflammatory reaction altogether. It is envisaged that the compositions of the present invention can be useful to prevent exacerbations in chronic inflammatory diseases.

It is to be understood explicitly that use of the compositions of the invention to treat inflammatory diseases does not include treatment of skin disorders or pain per se.

According to one aspect of the present invention there is provided a pharmaceutical composition comprising as an active ingredient a peptide according to Formula I: pGlu-$X_1$-$X_2$-$X_3$—OH, wherein $X_1$ is a polar amino acid residue; $X_2$ is an aromatic or hydrophobic amino acid residue; and $X_3$ is selected from a positively charged amino acid residue and a polar amino acid residue, or a pharmaceutically acceptable salt or derivative thereof; and a pharmaceutically acceptable carrier, for use in reducing the release or inhibiting the activity of an inflammatory cytokine.

According to some embodiments, $X_1$ is selected from the group consisting of: Asn, Gln, His, Ser, Thr, Tyr, and Cys, $X_2$ is selected from Trp, Phe, Tyr, Ala, Ile, Leu, Met, Val, and Gly and $X_3$ is selected from Lys, Lys derivative, Arg, His, Asn, Gln, His, Ser, Thr, and Tyr.

According to yet other embodiments, $X_1$ is selected from Asn and Thr; $X_2$ is selected from Trp, Phe and Tyr; and $X_3$ is selected from Lys, Lys derivative and Thr.

According to some embodiments, the peptide derivative comprises an alkyl group attached to a free functional group of the peptide sequence.

According to yet other embodiments, the alkyl group is attached by an amide bond or linkage to a free amino group of a side chain or the N-terminal of the peptide.

According to some embodiments, the alkyl a C4 to C30 alkyl.

According to some specific embodiments, a C8 alkyl group (herein octanoyl), is attached by an amide linkage to the side chain of a Lys residue of the peptide sequence or a terminal amino group of the peptide. According to some embodiments, the carboxy terminus of the peptide is modified, to form for example by an amide, alcohol or ester terminus, According to some specific embodiments, the peptide is selected from the group consisting of: pGlu-Asn-Trp-Lys(Octanoyl)-OH (SEQ ID NO: 1), pGlu-Asn-Trp-Thr-OH (SEQ ID NO: 2) and pharmaceutically acceptable derivatives and salts thereof.

According to some embodiments, the inflammatory cytokine is selected from the group consisting of: TNF alpha, IL-1 beta, IL-6, IL-10 and IFN gamma.

The present invention provides, according to yet another aspect, a pharmaceutical composition comprising as an active ingredient a peptide according to Formula I: pGlu-$X_1$-$X_2$-$X_3$—OH, wherein $X_1$ is a polar amino acid residue; $X_2$ is an aromatic or hydrophobic amino acid residue; and $X_3$ is selected from a positively charged amino acid residue and a polar amino acid residue, or a pharmaceutically acceptable salt or derivative thereof; and a pharmaceutically acceptable carrier, for use in reducing the release of an inflammatory mediator or chemokine, wherein the mediator or chemokine.

According to some specific embodiments, the peptide selected from the group consisting of: pGlu-Asn-Trp-Lys(Octanoyl)-OH (SEQ ID NO: 1), pGlu-Asn-Trp-Thr-OH (SEQ ID NO: 2) and pharmaceutically acceptable derivatives and salts thereof.

According to some embodiments, the inflammatory mediator or cytokine is selected from the group consisting of reactive oxygen species (ROS) and RANTES (Regulated upon activation normal T cell expressed and presumably secreted).

According to another aspect of the present invention there is provided a method of reducing the release or inhibiting the activity of at least one inflammatory or pro-inflammatory cytokine, the method comprising the step of administering to a subject in need thereof a therapeutically effective amount of a peptide according to Formula I: pGlu-$X_1$-$X_2$-$X_3$—OH, wherein $X_1$ is a polar amino acid residue; $X_2$ is an aromatic or hydrophobic amino acid residue; and $X_3$ is selected from a positively charged amino acid residue and a polar amino acid residue, or a pharmaceutically acceptable salt or derivative thereof.

According to another aspect, there is provided a method of reducing the release of an inflammatory mediator or chemokine, the method comprising the step of administering to a subject in need thereof a therapeutically effective amount of a peptide according to Formula I: pGlu-$X_1$-$X_2$-$X_3$—OH, wherein $X_1$ is a polar amino acid residue; $X_2$ is an aromatic or hydrophobic amino acid residue and $X_3$ is selected from a positively charged amino acid residue and a polar amino acid residue, or a pharmaceutically acceptable salt or derivative thereof.

According to some embodiments, the inflammatory mediator or chemokine is selected from the group consisting of ROS and RANTES.

According to yet another aspect, the present invention provides a method of treating an inflammatory disease or disorder. According to specific embodiments the inflammatory disease or disorder is selected from the group consisting of: an eye inflammatory disease or disorder, an ear inflammatory disease or disorder, a lung inflammatory disease or disorder, a bowel inflammatory disease or disorder, or an inflammatory autoimmune disease or disorder, the method comprising the step of administering to a subject in need thereof a therapeutically effective amount of a peptide according to Formula I: pGlu-$X_1$-$X_2$-$X_3$—OH, or a pharmaceutically acceptable salt or derivative thereof, wherein $X_1$ is a polar amino acid residue; $X_2$ is selected from an aromatic amino acid residue and a hydrophobic amino acid residue; and $X_3$ is selected from a positively charged amino acid residue and a polar amino acid residue.

According to some embodiments the present invention provides methods of treating chronic inflammatory diseases. According to specific embodiments the step of administering to a subject in need thereof a therapeutically effective amount of a peptide according to Formula I is performed even before the symptoms have emerged or developed. These methods of treating chronic inflammatory diseases are effective to prevent exacerbations.

According to yet another aspect, the present invention provides a method of treating an eye inflammatory disease or disorder, the method comprising the step of administering to a subject in need thereof a therapeutically effective amount of a peptide according to Formula I: pGlu-$X_1$-$X_2$-$X_3$—OH, or a pharmaceutically acceptable salt or derivative thereof, wherein $X_1$ is a polar amino acid residue; $X_2$ is an aromatic or hydrophobic amino acid residue and $X_3$ is selected from a positively charged amino acid residue and a polar amino acid residue.

According to some embodiments, $X_1$ is selected from the group consisting of: Asn, Gln, His, Ser, Thr, Tyr and Cys; $X_2$ is selected from Trp, Phe, Tyr, Ala, Ile, Leu, Met, Val, and Gly; and $X_3$ is selected from Lys, Lys derivative, Arg, His, Asn, Gln, His, Ser, Thr, and Tyr.

According to yet other embodiments, $X_1$ is selected from Asn and Thr; $X_2$ is selected from Trp, Phe and Tyr; and $X_3$ is selected from Lys, Lys derivative and Thr.

According to some specific embodiments, the Lys derivative is Lys(Octanoyl).

According to some embodiments, the peptide derivative comprises an alkyl group attached to a functional group of the peptide sequence.

According to yet other embodiments, the alkyl group is attached by an amide bond to an amino group of a side chain or a terminal of the peptide.

According to some embodiments, the alkyl is a C4 to C30 alkyl.

According to some specific embodiments, a C8 alkyl group (herein octanoyl), is attached by an amide bond to the side chain of a Lys residue or a terminal amino group of the peptide sequence.

According to some specific embodiments, the peptide is selected from the group consisting of: pGlu-Asn-Trp-Lys(Octanoyl)-OH (SEQ ID NO: 1), pGlu-Asn-Trp-Thr-OH (SEQ ID NO: 2) and pharmaceutically acceptable salts or derivatives thereof.

According to some embodiments, the peptide has an amino acid sequence as set forth in SEQ ID NO: 1.

According to some embodiments, the peptide has an amino acid sequence as set forth in SEQ ID NO: 2.

According to some embodiments, the pharmaceutical composition comprises a derivative or a salt of a peptide having an amino acid sequence set forth in a sequence selected from SEQ ID NO: 1 and SEQ ID NO: 2.

According to some embodiments, the method comprises administering a derivative or a salt of a peptide having an amino acid sequence set forth in a sequence selected from SEQ ID NO: 1 and SEQ ID NO: 2.

According to some embodiments, the pharmaceutical composition comprises a sodium salt of a peptide set forth in any one of SEQ ID NO: 1 and SEQ ID NO: 2.

According to some embodiments, the pharmaceutical composition is formulated for an administration via a route selected from the group consisting of: topical administration, ophthalmic administration, oral administration, nasal administration, and parenteral administration.

According to various embodiments, formulations for topical administration may be selected from a cream, an ointment, a paste, a lotion, a gel or in the form of eyedrops.

According to some specific embodiments, a cream formulation is provided comprising a peptide selected from SEQ ID NOs: 1 and 2, or a pharmaceutically acceptable salt thereof, for use in topical administration.

According to some embodiments, the cream composition comprises 0.1-5% w/w of the peptide. According to other embodiments, the composition comprises 0.5-2% of the peptide. According to yet other embodiments, the composition comprises about 1% of the peptide.

According to some embodiments, a composition according to the present invention, has a pH of about 4 to about 8. According to some embodiments, the composition has a pH of about 4.5 to about 6.5. According to yet other embodiments, the composition has a pH of about 7 to about 9.

According to some embodiments, the pharmaceutical composition comprises at least one excipient selected from the group consisting of: polysorbate 80, edetate disodium (EDTA), silicon dioxide, methylparaben, white petrolatum, isopropyl myristate, cetyl alcohol and glyceryl monostearate.

According to other embodiments, the composition for administration to a subject having a disease or injury of the eye is formulated in a form selected from the group consisting of a liquid solution or suspension for use as eyedrops, an emulsion, a cream, an ointment, a spray and a gel.

According to some embodiments, the disease or injury of the eye is an inflammatory disease or disorder selected from the group consisting of: uveitis, dry eye syndrome, inflammatory symptoms associated with an infectious eye disease, an allergic eye disease, keratitis, conjunctivitis, meibomian gland dysfunction and Sjogren syndrome.

According to still further embodiments, the pharmaceutical composition is formulated as eye drops, eye ointment, eye spray, ophthalmic suspension, ophthalmic emulsion, ophthalmic solution, ophthalmic gel, or intravitreal injection.

According to still further embodiments the inflammatory disease or disorder in an autoimmune disease or disorder.

According to still further embodiments the autoimmune disease or disorder is selected from the group consisting of rheumatoid arthritis, osteoarthritis, psoriatic arthritis, ankylosing spondylitis, juvenile idiopathic arthritis, lupus, and Sjogren syndrome.

According to still further embodiments the inflammatory disease or disorder is an inflammatory bowel disease.

According to still further embodiments the inflammatory bowel disease is selected from the group consisting of Crohn's disease, ulcerative colitis and celiac disease.

According to still further embodiments the inflammatory disease or disorder is an inflammatory disease or disorder of the lung.

According to still further embodiments the inflammatory disease or disorder of the lung is selected from the group consisting of asthma, bronchitis, pleurisy, alveolitis, vasculitis, pneumonia, chronic bronchitis, bronchiectasis, diffuse panbronchiolitis, hypersensitivity pneumonitis, idiopathic pulmonary fibrosis and cystic fibrosis.

According to still further embodiments the inflammatory disease or disorder is an inflammatory disease or disorder of the ear.

According to still further embodiments the inflammatory disease or disorder of the ear is selected from the group consisting of inflammatory symptoms associated with ear infection, otitis media, otitis externa, mastoiditis and otomastoiditis.

According to still further features embodiments the administration is ophthalmic administration.

According to still further embodiments the administration is oral administration.

According to still further embodiments the administration is nasal administration.

According to still further embodiments the administration is parenteral administration.

The present invention successfully addresses the shortcomings of the presently known configurations by providing pharmaceutical compositions for use in reducing the release or inhibiting the activity of inflammatory cytokines and mediators and for the treatment of diseases or disorders associated with inflammatory cytokines and mediators.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings.

DETAILED DESCRIPTION OF THE INVENTION

Figure 1:
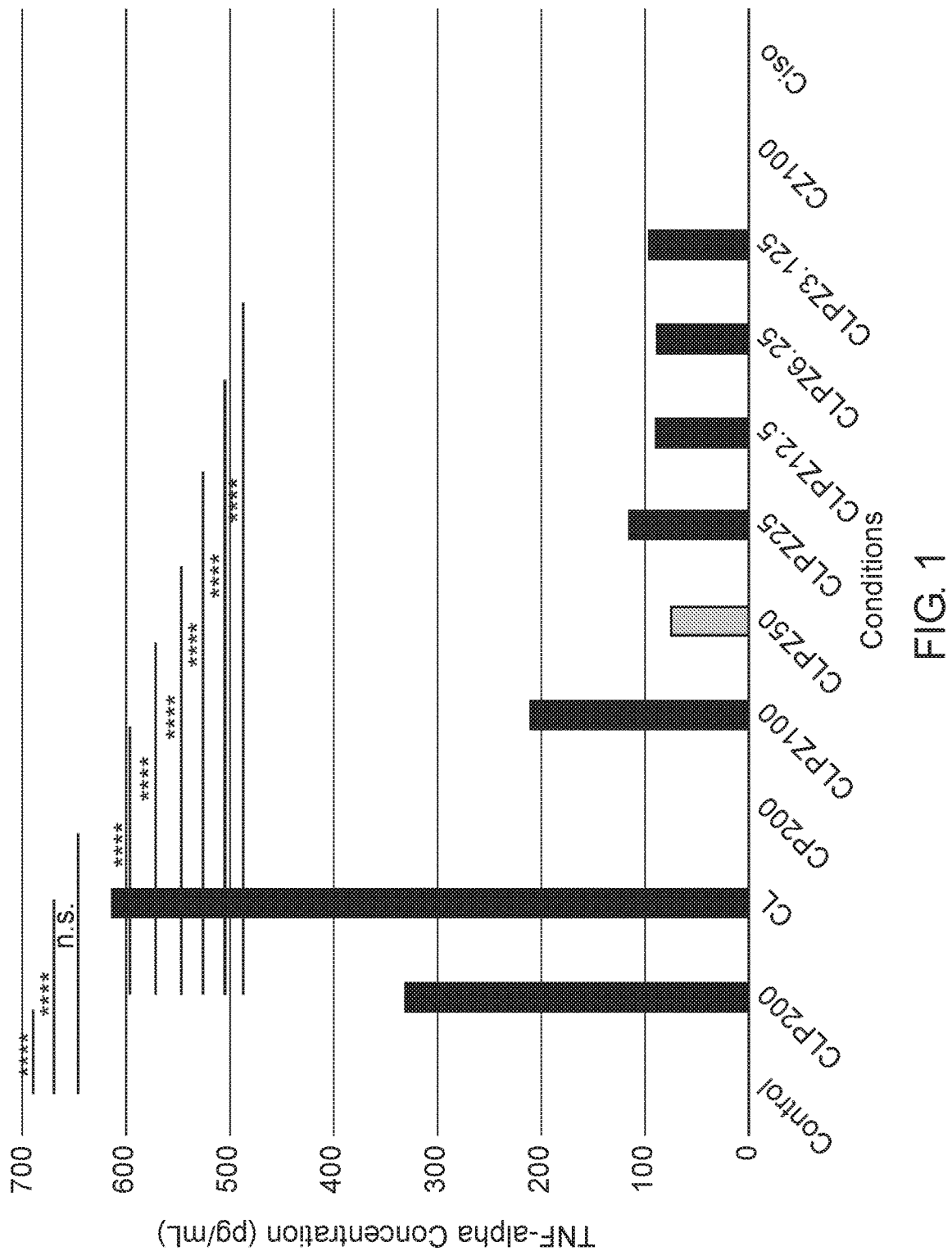
FIG. 1 is a bar graph illustrating the effect of ZEP4 (Z), concentration range: 3.125-100 µg/ml, on the amount of TNFα produced by inflammation-induced macrophage cells. Lines marked by **** represent statistically significant difference at $p<0.0001$.

The present invention, relates to pharmaceutical compositions comprising specific peptides and salts and derivatives thereof, for use in inhibiting inflammatory cascades. Inhibition of inflammatory mediators is beneficial in prevention and treatment of several inflammatory diseases and disorders, for example inflammatory diseases and disorders of the eye.

As exemplified herein the inhibitory effects on inflammatory cytokine release were demonstrated in-vitro in several models including mouse macrophage cell line, human monocytic cell line, human keratinocytes cell line, human peripheral blood monocytes (human PBMCs) and human corneal epithelial cells (HCEC), and in-vivo in an inflammatory atopic dermatitis (AD) mouse model.

The beneficial effect of the peptides on experimental corneal inflammation was demonstrated in a human corneal epithelial cell culture model.

The principles and operation of the present invention may be better understood with reference to the drawings and accompanying descriptions.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

While reducing the present invention to practice, the inventors have surprisingly uncovered that the peptides ZEP3 and ZEP4, and their sodium salt forms, reduced the expression of the inflammatory cytokines TNF alpha, IL-1 beta and IL-6 by macrophage and corneal epithelial cells, which had been induced for inflammation (Examples 1-7 below) and reduced the expression of IFN gamma, IL-10, IL-1 beta and RANTES in inflammatory-stimulated human PBMCs (Example 12 below). Furthermore, in an inflammatory model of atopic dermatitis in mice, ZEP4, ZEP3, and its sodium salt form ZEP3Na, significantly reduced clinical lesions in-vivo (Example 13 below). The results indicate that the peptides of the invention are uniquely capable of inhibiting or preventing inflammation.

Thus, according to one aspect of the present invention there is provided a pharmaceutical composition for reducing the release or inhibiting the activity of at least one cytokine or mediator involved in the etiology or pathology an inflammatory disease or disorder. The pharmaceutical composition includes a peptide as an active ingredient and a pharmaceutically acceptable carrier. The peptide has an amino acid sequence as set forth in any of SEQ ID Nos: 1 and 2, or a pharmaceutically acceptable salt thereof.

Accordingly, the present invention provides method for ameliorating and treating inflammatory pathologies associated with excess release or activity of specific cytokines and mediators.

According to some embodiments, the inflammatory pathology is a disease or disorder associated with excess release or activity of at least one cytokine or mediator, wherein the at least one cytokine or mediator is selected from the group consisting of: IFN-gamma, IL-1 beta, IL-10, TNF alpha, IL-6, ROS and RANTES.

The phrase "inflammatory disease or disorder" used herein refers to a disease, condition or disorder associated with inflammation. The term "inflammation" as used herein refers the process by which a subject's immune system coordinates a response to tissue damage, infection, antigenic challenge, etc. Inflammation may be associated with an increased blood supply to the tissue, increased capillary permeability in the tissue and/or increased leukocyte migration to the tissue.

Proinflammatory cytokines are produced predominantly by activated macrophages and are involved in the up-regulation of inflammatory reactions.

Inflammation may be diagnosed by elevated levels of inflammatory cytokines such as, but not limited to, TNFα, IL-1-alpha, IL-1-beta, IFN-gamma and IL-6 in a biological sample obtained from the subject. Biological sample may be, for example, tears, blood, serum, plasma, urine, sputum, saliva, faeces, semen, spinal fluid, bone marrow, lymph fluid, or CSF, the external secretions of the skin, respiratory, intestinal, and genitourinary tracts, milk, any human organ or tissue, any sample obtained by lavage, plural effusion, sample of in vitro or ex vivo cell culture and cell culture constituents.

Reactive oxygen species (ROS) are key signaling molecules that play an important role in the progression of inflammatory disorders. An enhanced ROS generation by polymorphonuclear neutrophils (PMNs) at the site of inflammation causes endothelial dysfunction and tissue injury. Under the inflammatory conditions, oxidative stress produced by PMNs leads to the opening of inter-endothelial junctions and promotes the migration of inflammatory cells across the endothelial barrier.

According to some embodiments of the present invention the inflammatory disease or disorder is an inflammatory disease or disorder of the eye. The inflammatory eye disease or disorder can be, but not limited to, uveitis, dry eye syndrome, inflammatory symptoms associated with a viral, bacterial or fungal eye infection, an allergic eye disease, keratitis, conjunctivitis, meibomian gland dysfunction and Sjogren syndrome.

In one embodiment the inflammatory disease or disorder of the eye is uveitis. The term "uveitis" as used herein refers to an inflammation of the uvea, which is the layer between the sclera and the retina, which includes the iris, ciliary body, and the choroid. Uveitis is also commonly referred to as iritis, pars planitis, chroiditis, chorioretinitis, anterior uveitis, and posterior uveitis. The most common form of uveitis is anterior uveitis, which involves inflammation in the front part of the eye, which is usually isolated to the iris. This condition is often called iritis.

In one embodiment the inflammatory disease or condition of the eye is dry eye syndrome. The phrase "dry eye syndrome (DES)" used herein refers to a condition of altered tear composition that results from a diseased or dysfunctional lacrimal functional unit. Evidence suggests that inflammation causes structural alterations of the tear-secreting glands. Changes in tear composition resulting from lacrimal dysfunction, increased evaporation and/or poor clearance have pro-inflammatory effects on the ocular surface. This inflammation is responsible in part for the irritation symptoms, ocular surface epithelial disease, and altered corneal epithelial barrier function in dry eye. Anti-inflammatory therapies for DES target one or more of the inflammatory mediators/pathways that have been identified in dry eye. DES is also known by those in the art as dry eye disease (DED), keratoconjunctivitis sicca and keratitis sicca.

In one embodiment the inflammatory disease or condition of the eye is associated with Sjogren's syndrome. The phrase "Sjogren's syndrome" as used herein refers to a systemic autoimmune inflammatory disorder characterized by decreased tearing, dry mouth and other dry mucous membranes, and is often associated with autoimmune rheumatic disorders, such as rheumatoid arthritis. Dryness of the eyes and mouth are the most common symptoms of this syndrome. The symptoms may occur alone, or with symptoms associated with rheumatoid arthritis or other connective tissue diseases. There may be an associated enlargement of the salivary glands. Other organs may become affected. The syndrome may be associated with rheumatoid arthritis, systemic lupus erythematosus (SLE), scleroderma, polymyositis, and other diseases.

In some embodiments the inflammatory disease or condition of the eye is resulting from a procedure involving the eye, e.g., corneal transplantation/keratoplasty, keratoprosthesis surgery, lamellar transplantation, or selective endothelial transplantation.

In some embodiments the inflammatory disease or condition of the eye is affecting the surface of the eye such as, but not limited to, corneal ocular surface inflammatory conditions, corneal neovascularization, keratitis, including peripheral ulcerative keratitis and microbial keratitis, conjunctivitis, or pemphigoid syndrome.

In some embodiments the inflammatory disease or condition of the eye is an autoimmune disorder affecting the eye such as, but not limited to, sympathetic ophtahlmia, Vogt-Koyanagi Harada (VKH) syndrome, birdshot retinochoriodopathy, ocular cicatricial pemphigoid (OCP), Sjogren syndrome or Fuchs' heterochronic iridocyclitis.

According to some embodiments of the present invention the inflammatory disease or disorder is an autoimmune disease or disorder. The autoimmune disease or disorder can be, but not limited to, rheumatoid arthritis, osteoarthritis, psoriatic arthritis, pemphigus vulgaris, ankylosing spondylitis, juvenile idiopathic arthritis, lupus and Sjogren syndrome.

In one embodiment the autoimmune disease or disorder is rheumatoid arthritis. The phrase "rheumatoid arthritis" as used herein refers to a chronic, autoimmune disorder in which multiple joints are inflamed. Inflammation of the synovial joint lining is accompanied by joint pain and stiffness and usually leads to bone and joint destruction, deformity, disability, and even death.

In one embodiment the autoimmune disease or disorder is lupus. The term "lupus" as used herein refers to a chronic, inflammatory autoimmune disorder called lupus erythematosus that may affect many organ systems including the skin, joints and internal organs. Lupus is a general term which includes a number of specific types of lupus, including systemic lupus, lupus nephritis, and lupus cerebritis. In systemic lupus (SLE), the body's natural defenses are turned against the body and rogue immune cells attack the body's tissues. Antibodies may be produced that can react against the body's blood cells, organs, and tissues. This reaction leads to immune cells attacking the affected systems, producing a chronic disease. Lupus nephritis, also referred to as lupus glomerular disease, is kidney disorder that is usually a complication of SLE, and is characterized by damage to the glomerulus and progressive loss of kidney function. Lupus cerebritis refers to another complication of SLE, which is inflammation of the brain and/or central nervous system.

In one embodiment of the present invention the inflammatory disease or disorder is osteoarthritis (OA). OA is also referred to as hypertrophic osteoarthritis, osteoarthrosis, and degenerative joint disease. OA is a chronic degenerative disease of skeletal joints, which affects specific joints, commonly knees, hips, hand joints and spine, in adults of all ages. OA is characterized by a number of the following manifestations including degeneration and thinning of the articular cartilage with associated development of "ulcers" or craters, osteophyte formation, hypertrophy of bone at the margins, and changes in the synovial membrane and enlargement of affected joints. Furthermore, osteoarthritis is accompanied by pain and stiffness, particularly after prolonged activity. The peptides, salts and derivatives thereof and pharmaceutical compositions comprising them, of the invention can be used to treat osteoarthritis. Characteristic radiographic features of osteoarthritis include joint space narrowing, subchondral sclerosis, osteophytosis, subchondral cyst formation, loose osseous body (or "joint mouse").

According to some embodiments of the present invention the inflammatory disease or disorder is an inflammatory bowel disease. The inflammatory bowel disease can be, but not limited to, Crohn's disease, ulcerative colitis and celiac disease.

According to some embodiments of the present invention the inflammatory disease or disorder is an inflammatory disease or disorder of the lung. The inflammatory disease or disorder of the lung can be, but not limited to, asthma, bronchitis, pleurisy, alveolitis, vasculitis, pneumonia, chronic bronchitis, bronchiectasis, diffuse panbronchiolitis, hypersensitivity pneumonitis, idiopathic pulmonary fibrosis and cystic fibrosis.

According to some embodiments of the present invention the inflammatory disease or disorder is an inflammatory disease or disorder of the ear. The inflammatory disease or disorder of the ear can be, but not limited to, inflammatory symptoms associated with ear infection, otitis media, otitis externa, mastoiditis and otomastoiditis.

The present invention also provides a pharmaceutical composition for use in treating a disease or disorder associates with excess release of inflammatory mediators and chemokines, including but not limited to ROS, RANTES and monocyte chemotactic protein-1 (MCP-1). Inflammatory diseases associated with release of ROS that are treatable with the compositions of the present invention, include but are not limited to lung diseases, cardiovascular diseases, Kidney Disease-Related Vascular Calcification and inflammatory metabolic diseases.

The chemokines RANTES and MCP-1 are involved in lung allergic inflammation, lung leukocyte infiltration, bronchial hyperresponsiveness, and the recruitment of eosinophils in the pathogenesis of asthma.

The term "treatment" or "treating" may be used interchangeably herein refers to inhibiting, preventing or arresting the development of a disease or disorder and/or causing the reduction, remission, or regression of a disease or disorder.

The peptides, derivatives and salts used in the compositions and methods of the present invention may be synthesized using any method known in the art, including but not limited to solid phase and liquid phase peptide synthesis. Some of the peptides used in the compositions of the present invention may be produced using recombinant methods or combination of recombinant and synthetic methods.

In one embodiment of the present invention the peptide is of pGlu-Asn-Trp-Lys (Octanoyl)-OH (SEQ ID NO: 1; hereinafter referred to as "ZEP3"), wherein pGlu is pyroglutamic acid. The peptide ZEP3 can be produced, for example, by the procedure described in U.S. Pat. No. 7,220,725.

In one embodiment of the present invention the peptide is pGlu-Asn-Trp-Thr-OH (SEQ ID NO: 2; hereinafter referred to as "ZEP4"). The peptide ZEP4 can be produced, for example, by the following procedure:

The synthesis of the peptide ZEP4 is carried out by a sequential synthesis of 9-fluoromethoxycarbonyl (Fmoc) amino acids on a solid support of Chlorotrityl chloride resin (CTC). CTC resin (125 gr) is loaded with Fmoc-Threonine (t-butyl; 79 gr) and Diisopropyl amine (DIPEA; 160 gr) served as the coupling agent of the amino acid to the solid support. The Fmoc protecting group is removed by a mixture of 25% piperidine and the resin-peptide is filtered and washed with Dimethylformamide (DMF). A second amino acid, Fmoc-Trp (85 gr), is activated by a mixture of 3-[Bis (dimethylamino) methyl iumyl]-3H-benzotriazol-1-oxide, Hexafluorophosphate (HBTU)/hydroxy benzothiazole (OHBT)] coupled to the first amino acid by addition of DIEA. The Fmoc group is removed as described hereinabove and the resin-peptide is filtered and washed with Dimethylformamide (DMF). A third amino acid, Fmoc-Asn (trt) (119 gr) is activated by HBTU/HOBT and coupled by addition of DIEA. The Fmoc group is removed as described hereinabove and the resin-peptide is filtered and washed with Dimethylformamide (DMF). A fourth amino acid pGlu (26 gr) is activated by HBTU/HOBT and coupled by DIEA.

The peptide-resin is thoroughly washed with DMF followed by IPA and dried under reduced pressure. The peptide is cleaved from the resin and protecting groups of the Thr and Asn as well by TFA (95%) and Triisopropyl silane (TIS) (5%) at room temperature for 2 hr. The peptide is precipitated by addition of methyl tert-butyl ether (MTBE), filtered and dried (yield 46 gr).

The crude product (46 gr) is dissolved in a mixture of acetonitrile (ACN)/water and loaded on preparative HPLC system (4", RP C-18 100-120 A pore size) and purified using a gradient system consisting of: Phase A—0.1% TFA in water; and Phase B—ACN. The elution is done by gradually increasing phase B (3% to 33%) during 45 min. Fractions having purity greater than 97% are collected. The combined fractions are eluted on the same HPLC system using a gradient consisting of: Phase A: 0.2% Acetic acid; and Phase B: ACN. The elution is done by gradually increasing phase B (10% to 40%) during 30 min. Fractions having purity greater than 97% are collected combined and lyophilized (yield 29 gr). The final product has M.W (MS) of 530.5; and 97.3% purity (HPLC).

Also included within the scope of the invention are salts and derivatives of the peptides used in the disclosed compositions and methods.

As used herein the term "salts" refers to both salts of carboxyl groups and to acid addition salts of amino or guanidino groups of the peptide molecule. Salts of carboxyl groups may be formed by means known in the art and include inorganic salts, for example sodium, calcium, ammonium, ferric or zinc salts, and the like, and salts with organic bases such as salts formed for example with amines such as triethanolamine, piperidine, procaine, and the like. Acid addition salts include, for example, salts with mineral acids such as, for example, acetic acid or oxalic acid. Salts describe here also ionic components added to the peptide solution to enhance hydrogel formation and/or mineralization of calcium minerals.

"Derivatives" of the peptides of the invention as used herein covers derivatives which may be prepared from the functional groups which occur as side chains on the residues or the N- or C-terminal groups, by means known in the art, and are included in the invention as long as they remain pharmaceutically acceptable, i.e., they do not destroy the activity of the peptide, do not confer toxic properties on compositions containing it, and do not adversely affect the immunogenic properties thereof.

These derivatives may include, for example, aliphatic esters of the carboxyl groups, amides of the carboxyl groups produced by reaction with ammonia or with primary or secondary amines, N-acyl derivatives of free amino groups of the amino acid residues formed by reaction with acyl moieties (e.g., alkanoyl or aroyl groups), or O-acyl derivatives of free hydroxyl group (e.g., that of seryl or threonyl residues) formed by reaction with acyl moieties.

In one embodiment of the present invention the peptide is the sodium salt of the peptide set forth in SEQ ID NO: 1 (pGlu-Asn-Trp-Lys(Octanoyl)-OH.nNa wherein n is 1 or 2; hereinafter referred to as "ZEP3 sodium salt" or ZEP3Na).

ZEP3 sodium salt can be produced, for example, by the following procedure: ZEP3 (3.1 g) is solubilized in $NaHCO_3$ (100 mM) in water (50 g/l). The solution is injected into an HPLC ion exchange column (2.5×22 cm Luna C18, 100 A, 15 micron) and eluted by a gradient consisting of: Mobile Phase A: $NaHCO_3$ 2 mM in $H_2O$; Mobile Phase B: $NaHCO_3$ 2 mM in $CH_3CN/H_2O$ (8/2); and Mobile Phase C: $NaHCO_3$ 100 mM in water. Loading per run: 5% maximum (W/W % PEPTIDE/STATIONARY PHASE). Flow: 4.8 cm/min (24 ml/min). The gradient procedure is as follows: 20 min phase C; 5 min Phase A; 18 min Phase B; and 7 min Phase C. A fraction containing the product is collected and concentrated under reduced pressure to remove acetonitrile (110 g/l) then freeze dried [yield 2.2 g (71%)]. The final product has 99.7% purity (HPLC), 3.1% sodium content and solubility of 50 mg/ml water.

In one embodiment of the present invention the peptide is the sodium salt of the peptide set forth in SEQ ID NO: 2 (pGlu-Asn-Trp-Thr-OH.nNa wherein n is 1 or 2; hereinafter referred to as "ZEP4 sodium salt" or ZEP4Na). ZEP4 sodium salt can be produced, for example, by the following procedure:

ZEP4 (5 g) is solubilized in $NaHCO_3$ (100 mM) in water (50 g/l). The solution is injected into an HPLC ion exchange column (2.5×22 cm Luna C18, 100 A, 15 micron) and eluted by a gradient consisting of: Mobile Phase A: $NaHCO_3$ 2 mM in H2O; Mobile Phase B: $NaHCO_3$ 2 mM in $CH_3CN/H_2O$ (8/2); and Mobile Phase C: $NaHCO_3$ 100 mM in water. Loading per run: 5% maximum (W/W % PEPTIDE/STATIONARY PHASE). Flow: 4.8 cm/min (24 ml/min). The gradient procedure is as follows: 20 min phase C, then 5 min Phase A, then 20 min Phase B and 10 min Phase C. A fraction containing the product is collected and concentrated under reduced pressure to remove acetonitrile (110 g/l) then freeze dried [yield 4 g (80%]. The final product has 97.5% purity (HPLC), 2.5% sodium content and solubility of 50 mg/ml water.

The peptides of the present invention can be used in therapy per se or as part (active ingredient) of a pharmaceutical composition.

As used herein a "pharmaceutical composition" refers to a preparation of one or more of the active ingredients described herein with other chemical components such as physiologically suitable carriers and excipients. The purpose of a pharmaceutical composition is to facilitate administration of a compound to an organism.

Hereinafter, the phrases "physiologically acceptable carrier" and "pharmaceutically acceptable carrier" which may be interchangeably used refer to a carrier or a diluent that does not cause significant irritation to an organism and does not abrogate the biological activity and properties of the administered compound. An adjuvant is included under these phrases.

Herein the term "excipient" refers to an inert substance added to a pharmaceutical composition to further facilitate administration of an active ingredient. Examples, without limitation, of excipients include calcium carbonate, calcium phosphate, various sugars and types of starch, polysugars, cyclodextrins, suspending agents like polyvinypyrrolidone, polyvinyl alcohol, ionic or non-ionic surfactants, solubilizers, emulsifiers such as lecithin, penetration enhancers, polycarboxylic acids, cellulose derivatives, gelatin, vegetable oils, waxes, mineral oils, propyleneglycol and polyethylene glycols.

Techniques for formulation and administration of drugs may be found in "Remington's Pharmaceutical Sciences," Mack Publishing Co., Easton, Pa., latest edition, which is incorporated herein by reference.

Suitable routes of administration may, for example, include ophthalmic, topical, oral, rectal, transmucosal, transnasal, intestinal, or parenteral delivery, including intramuscular, subcutaneous and intramedullary injections as well as intrathecal, direct intraventricular, intravenous, inrtaperitoneal, intranasal, or intraocular injections.

Pharmaceutical compositions of the present invention may be manufactured by processes well known in the art, e.g., by means of conventional mixing, dissolving, suspending, solubilizing, granulating, dragee-making, levigating, emulsifying, encapsulating, entrapping, spray-drying, or lyophilizing processes.

Pharmaceutical compositions for use in accordance with the present invention thus may be formulated in conventional manner using one or more physiologically acceptable carriers comprising excipients and auxiliaries, which facilitate processing of the active ingredients into preparations which can be used pharmaceutically. Proper formulation is dependent upon the route of administration chosen.

The pharmaceutical composition described herein may be formulated for ophthalmic administration. The phrase "ophthalmic administration" used herein refers to administration of the peptide or the pharmaceutical composition of the invention in the external eye (e.g., conjunctival sac) or intravitreally. Dosage forms suitable for ophthalmic administration can be, but not limited to, eye drops, eye ointment, eye spray, ophthalmic suspension, ophthalmic emulsion, ophthalmic solution, ophthalmic gel, or intravitreal injection.

The pharmaceutical composition described herein may be formulated for topical administration. Dosage forms suitable for topical administration can be, but not limited to, liquid drops, liquid wash, gel, ointment, emulsion, suspension, lotion, spray, nebulized liquid, suppository, cream, powder, foam, crystals and liposomes.

For injection, the active ingredients of the pharmaceutical composition may be formulated in aqueous solutions, preferably in physiologically compatible buffers such as Hank's solution, Ringer's solution, or physiological salt buffer. One route of administration which is suited for the pharmaceutical compositions of the present invention is sub-periosteal injection, as described in U.S. Pat. No. 6,525,030 to Erikkson. For transmucosal administration, penetrants appropriate to the barrier to be permeated are used in the formulation. Such penetrants are generally known in the art.

For oral administration, the pharmaceutical composition can be formulated readily by combining the active compounds with pharmaceutically acceptable carriers well known in the art. Such carriers enable the pharmaceutical composition to be formulated as tablets, pills, dragees, capsules, liquids, gels, syrups, slurries, suspensions, emulsions, and the like, for oral ingestion by a patient. Pharmacological preparations for oral use can be made using a solid excipient, optionally grinding the resulting mixture, and processing the mixture of granules, after adding suitable auxiliaries if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carbomethylcellulose; and/or physiologically acceptable polymers such as polyvinylpyrrolidone (PVP). If desired, disintegrating agents may be added, such as cross-linked polyvinyl pyrrolidone, agar, or alginic acid or a salt thereof such as sodium alginate. As used herein, the term "oral administration" includes administration of the pharmaceutical compound to any oral surface, including the tongue, gums, palate, sublingual, or other buccal surfaces.

Dragee cores are provided with suitable coatings. For this purpose, concentrated sugar solutions may be used which may optionally contain gum arabic, talc, polyvinyl pyrrolidone, carbopol gel, polyethylene glycol, titanium dioxide, lacquer solutions and suitable organic solvents or solvent mixtures. Dyestuffs or pigments may be added to the tablets or dragee coatings for identification or to characterize different combinations of active compound doses.

Pharmaceutical compositions which can be used orally, include push-fit capsules made of gelatin as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate and, optionally, stabilizers. In soft capsules, the active ingredients may be dissolved or suspended in suitable liquids, such as fatty oils, liquid paraffin, or liquid polyethylene glycols. In addition, stabilizers may be added. All formulations for oral administration should be in dosages suitable for the chosen route of administration.

For buccal administration, the compositions may take the form of tablets or lozenges formulated in conventional manner.

For administration by nasal inhalation, the active ingredients for use according to the present invention are conveniently delivered in the form of an aerosol spray presentation from a pressurized pack or a nebulizer with the use of a suitable propellant, e.g., dichlorodifluoromethane, trichlorofluoromethane, dichloro-tetrafluoroethane or carbon dioxide. In the case of a pressurized aerosol, the dosage unit may be determined by providing a valve to deliver a metered amount. Capsules and cartridges of, e.g., gelatin for use in a dispenser may be formulated containing a powder mix of the compound and a suitable powder base such as lactose or starch.

The pharmaceutical composition described herein may be formulated for parenteral administration, e.g., by bolus injection or continuous infusion. Formulations for injection may be presented in unit dosage form, e.g., in ampoules or in multidose containers with optionally, an added preservative. The compositions may be suspensions, solutions or emulsions in oily or aqueous vehicles, and may contain formulatory agents such as solubilizing, suspending, stabilizing and/or dispersing agents.

Pharmaceutical compositions for parenteral administration include aqueous solutions of the active preparation in water-soluble form. Additionally, suspensions of the active ingredients may be prepared as appropriate oily or water-based injection suspensions. Suitable lipophilic solvents or vehicles include fatty oils such as sesame oil, or synthetic fatty acids esters such as ethyl oleate, triglycerides emulsions or liposomes. Aqueous injection suspensions may contain substances, which increase the viscosity of the suspension, such as sodium carboxymethyl cellulose, sorbitol or dextran. Optionally, the suspension may also contain suitable stabilizers or agents which increase the solubility of the active ingredients to allow for the preparation of highly concentrated solutions.

Alternatively, the active ingredient may be in powder form for constitution with a suitable vehicle, e.g., sterile, pyrogen-free water-based solution, before use.

The pharmaceutical composition of the present invention may also be formulated in rectal compositions such as suppositories or retention enemas, using, e.g., conventional suppository bases such as cocoa butter or other glycerides.

Pharmaceutical compositions suitable for use in context of the present invention include compositions wherein the active ingredients are contained in an amount effective to achieve the intended purpose. More specifically, a therapeutically effective amount means an amount of active ingredients effective to prevent, alleviate or ameliorate symptoms of a disease or disorder of the subject being treated.

Determination of a therapeutically effective amount is well within the capability of those skilled in the art, especially in light of the detailed disclosure provided herein.

For any preparation used in the methods of the invention, the therapeutically effective amount or dose can be estimated initially from in vitro and cell culture assays. For example, a dose can be formulated in an animal model to achieve a desired concentration or titer. Such information can be used to more accurately determine useful doses in humans.

Toxicity and therapeutic efficacy of the active ingredients described herein can be determined by standard pharmaceutical procedures in vitro, in cell cultures or experimental animals. The data obtained from these in vitro and cell culture assays and animal studies can be used in formulating a range of dosage for use in human. The dosage may vary depending upon the dosage form employed and the route of administration utilized. The exact formulation, route of administration and dosage can be chosen by the individual physician in view of the patient's condition. (See e.g., Fingl, et al., 1975, in "The Pharmacological Basis of Therapeutics", Ch. 1 p. 1).

Dosage amount and interval may be adjusted individually to levels of the active ingredient which are sufficient to achieve the minimal effective concentration (MEC). The MEC will vary for each preparation but can be estimated from in vitro data. Dosages necessary to achieve the MEC will depend on individual characteristics and route of administration. Detection assays can be used to determine plasma or tissue concentrations.

Depending on the severity and responsiveness of the condition to be treated, dosing can be of a single or a plurality of administrations, with course of treatment lasting from several days to several weeks or diminution of the disease state is achieved.

The amount of a composition to be administered will, of course, be dependent on the subject being treated, the severity of the affliction, the manner of administration, the judgment of the prescribing physician, etc.

Thus, compositions and/or articles of some embodiments of the invention may, if desired, be presented in a pack or dispenser device, such as an FDA approved kit, which may contain one or more unit-dosage forms containing the active ingredient. The pack may, for example, comprise metal or plastic foil, such as a blister pack. The pack or dispenser device may be accompanied by instructions for administration. The pack or dispenser may also be accommodated by a notice associated with the container in a form prescribed by a governmental agency regulating the manufacture, use or sale of pharmaceuticals, which notice is reflective of approval by the agency of the form of the compositions or human or veterinary administration. Such notice, for example, may be of labeling approved by the U.S. Food and Drug Administration for prescription drugs or of an approved product insert. Compositions comprising a preparation of the invention formulated in a compatible pharmaceutical carrier may also be prepared, placed in an appropriate container (e.g., lyophilized vial), and labeled for treatment of an indicated condition, as is further detailed above.

The peptide or the pharmaceutical composition of the present invention can be used to inhibit the release or activity of inflammatory cytokines and mediators and to treat an inflammatory disease or disorder by providing a subject in need thereof with a therapeutically effective amount of the peptide or the pharmaceutical composition.

The phrase "subject in need thereof" used herein refers to a mammalian male or female subject (e.g., human being) who is diagnosed with an inflammatory disease or disorder. In a specific embodiment, this term encompasses individuals who are at risk to develop an inflammatory disease or disorder. The subject may be of any gender or at any age including neonatal, infant, juvenile, adolescent, adult and elderly adult.

As used herein the term "about" refers to ±10%.

The terms "comprises", "comprising", "includes", "including", "having" and their conjugates mean "including but not limited to".

The term "consisting of means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions, illustrate the invention in a non-limiting fashion.

Example 1—the Effect of ZEP4 on the Expression of TNF Alpha by Inflammation-Induced Macrophage Cells Materials and Methods The peptide pGlu-Asn-Trp-Thr-OH (hereinafter referred to as "ZEP4", SEQ ID NO: 2) was synthesized as described hereinabove.

Expression of TNF Alpha by B6 Macrophage Cells

Macrophages originating from C57BL/6 mice were cultured at a density of 200,000 cells/mL in a 24-well plate (500 µl wells) and incubated at 37° C. and 5% $CO_2$ overnight. Following incubation, culture media in certain experimental groups were replaced with fresh media containing 100 ng/mL LPS, followed by three hours incubation. Then, the media (LPS-containing or LPS-free) in certain experimental groups were replaced with fresh media containing ZEP4 at concentrations ranging from 3.125 to 100 µg/ml, followed by one-hour incubation. Next, palmitic acid (PA, 200 µM) was added to the appropriate wells and the plates were incubated for additional 24 hours, then the amount of TNF alpha in each well was measured. Table 1 lists the different treatment and control groups. Reduction in TNF alpha production in the treatment groups was calculated relative to cells treated with LPS and PA (CLP200).

Results

FIG. 1 and Table 1 below show that ZEP4 substantially reduced the amount of TNF alpha produced by the inflammation-induced macrophage cells treated with LPS and Palmitic Acid for 24 hr. ZEP4 concentration of 3.125 µg/ml caused 70.6% reduction in TNF alpha expression. The most effective concentration of ZEP4 was 50 µg/ml, which caused a 77.0% reduction in TNF alpha expression (p<0.0001).

Example 2—the Effect of ZEP4 on the Expression of TNF Alpha by Inflammation-Induced Macrophage Cells Materials and Methods The peptide ZEP4 (SEQ ID NO: 2), was synthesized as described hereinabove.

Expression of TNF Alpha by B6 Macrophage Cells

Macrophages originating from C57BL/6 mice were cultured at a density of 200,000 cells/mL in a 24-well plate (500 µl wells) and incubated at 37° C. and 5% $CO_2$ overnight. Following incubation, media were replaced with fresh media containing 100 ng/mL LPS, followed by three hours incubation. The LPS-containing media in the treatment groups were then replaced with fresh media containing ZEP4 at 50 µg/ml, followed by one-hour incubation. Then, aliquots of palmitic acid (100, 200 or 400 µM) were added to appropriate wells. The plates were incubated for additional 24 hour and the amount of TNF alpha in each well was measured. Table 2 lists the different treatment and control groups. Reduction in TNF alpha production in the treatment groups was calculated relative to cells treated with LPS and PA, according to the PA concentration.

Results

Figure 2:
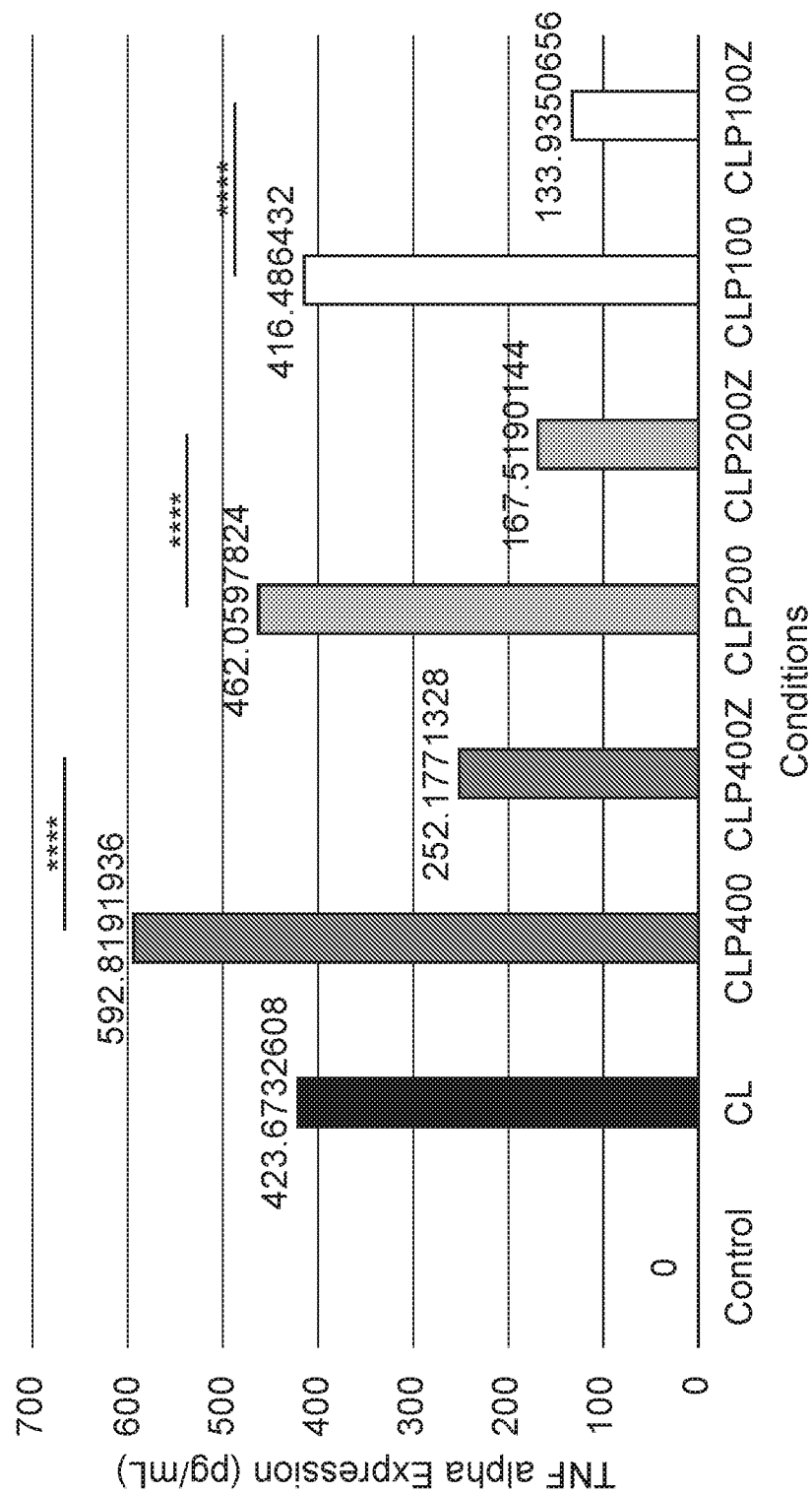
FIG. 2 is a bar graph illustrating the effect of ZEP4 (Z), (50 µg/ml) on the amount of TNFα produced by inflammation-induced macrophage cells, treated with lipopolysaccharide (LPS, 100 ng/ml) and palmitic acid (PA, 100, 200 or 400 μM). Lines marked by **** represent statistically significant difference at p<0.0001.

FIG. 2 and Table 2 below show that palmitic acid concentrations of 100, 200 and 400 µM induced macrophages TNF alpha expression of 416, 462 and 593 µg/mL, respectively. ZEP4 at a concentration of 50 µg/ml substantially reduced TNF alpha expression by macrophages under all palmitic acid concentrations (****p<0/0001).

TABLE 2

The effect of ZEP4 (50 µg/ml) on the expression of TNF alpha by macrophages treated with LPS (100 ng/ml) and palmitic acid (100, 200 and 400 µM).

| Treatment | ZEP4 (µg/ml) | LPS (ng/ml) | palmitic acid (µM) | TNF alpha (pg/ml) | % reduction of TNF alpha |
|---|---|---|---|---|---|
| Control | Negative control | — | — | 0 | — |

TABLE 1

The effect of ZEP4 concentration on the expression of TNF alpha by macrophages treated with LPS and Palmitic Acid

| Treatment | Mark | ZEP4 (µg/ml) | LPS (ng/mL) | palmitic acid (µM) | TNF alpha (pg/mL) | % reduction of TNF alpha |
|---|---|---|---|---|---|---|
| Negative control (cells) | Control | — | — | — | 0 | — |
| LPS and Palmitic acid control | CLP200 | — | 100 | 200 | 332.39 | — |
| LPS control | CL | — | 100 | — | 613.81 | — |
| Palmitic acid control | CP200 | — | — | 200 | 0 | — |
| ZEP4-100 | CLPZ100 | 100 | 100 | 200 | 211.68 | 36.3 |
| ZEP4-50 | CLPZ50 | 50 | 100 | 200 | 76.23 | 77.0 |
| ZEP4-25 | CLPZ25 | 25 | 100 | 200 | 115.58 | 65.2 |
| ZEP4-12.5 | CLPZ12.5 | 12.5 | 100 | 200 | 93.12 | 72.0 |
| ZEP4-6.25 | CLPZ6.25 | 6.25 | 100 | 200 | 89.83 | 73.0 |
| ZEP4-3.125 | CLPZ3.125 | 3.125 | 100 | 200 | 97.79 | 70.6 |
| ZEP4 control | CZ100 | 100 | — | — | 0 | — |
| Isopropanol vehicle control | Ciso | — | — | — | 0 | — |

TABLE 2-continued

The effect of ZEP4 (50 µg/ml) on the expression of TNF alpha by macrophages treated with LPS (100 ng/ml) and palmitic acid (100, 200 and 400 µM).

| Treatment | ZEP4 (µg/ml) | LPS (ng/ml) | palmitic acid (µM) | TNF alpha (pg/ml) | % reduction of TNF alpha |
|---|---|---|---|---|---|
| CL | — | 100 | — | 423.67 | — |
| CLP400 | — | 100 | 400 | 592.82 | — |
| CLP400Z | 50 | 100 | 400 | 252.177 | 57.5**** |
| CLP200 | — | 100 | 200 | 462.06 | — |
| CLP200Z | 50 | 100 | 200 | 167.52 | 63.7**** |
| CLP100 | — | 100 | 100 | 416.48 | — |
| CLP100Z | 50 | 100 | 100 | 133.93 | 67.8**** |

Example 3—the Effect of ZEP3 on the Expression of TNF Alpha by Inflammation-Induced Macrophage Cells Materials and Methods The peptide pGlu-Asn-Trp-Lys(Octanoyl)-OH (hereinafter referred to as "ZEP3", SEQ ID NO: 1) was synthesized as described in U.S. Pat. No. 7,220,725.

Expression of TNF Alpha by B6 Macrophage Cells

Macrophage cells originating from C57BL/6 mice were cultured at a density of 200,000 cells/mL in a 24-well plate (500 µl wells) and incubated at 37° C. and 5% $CO_2$ overnight. Following incubation, media in certain experimental groups were replaced with fresh media containing 100 ng/mL LPS, followed by three hours incubation. Then, the media (LPS-containing or LPS-free) in certain experimental groups were replaced with fresh media containing ZEP3 at a concentration ranging from 3.125 to 100 µg/ml, followed by one-hour incubation. Next, palmitic acid (200 µM) aliquots were added to the appropriate wells and the plates were incubated for additional 24 hours, then the amount of TNF alpha in each well was measured. Table 3 lists the different treatment and control groups. Reduction in TNF alpha production in the treatment groups was calculated relative to cells treated with LPS and PA.

Results

Figure 3:
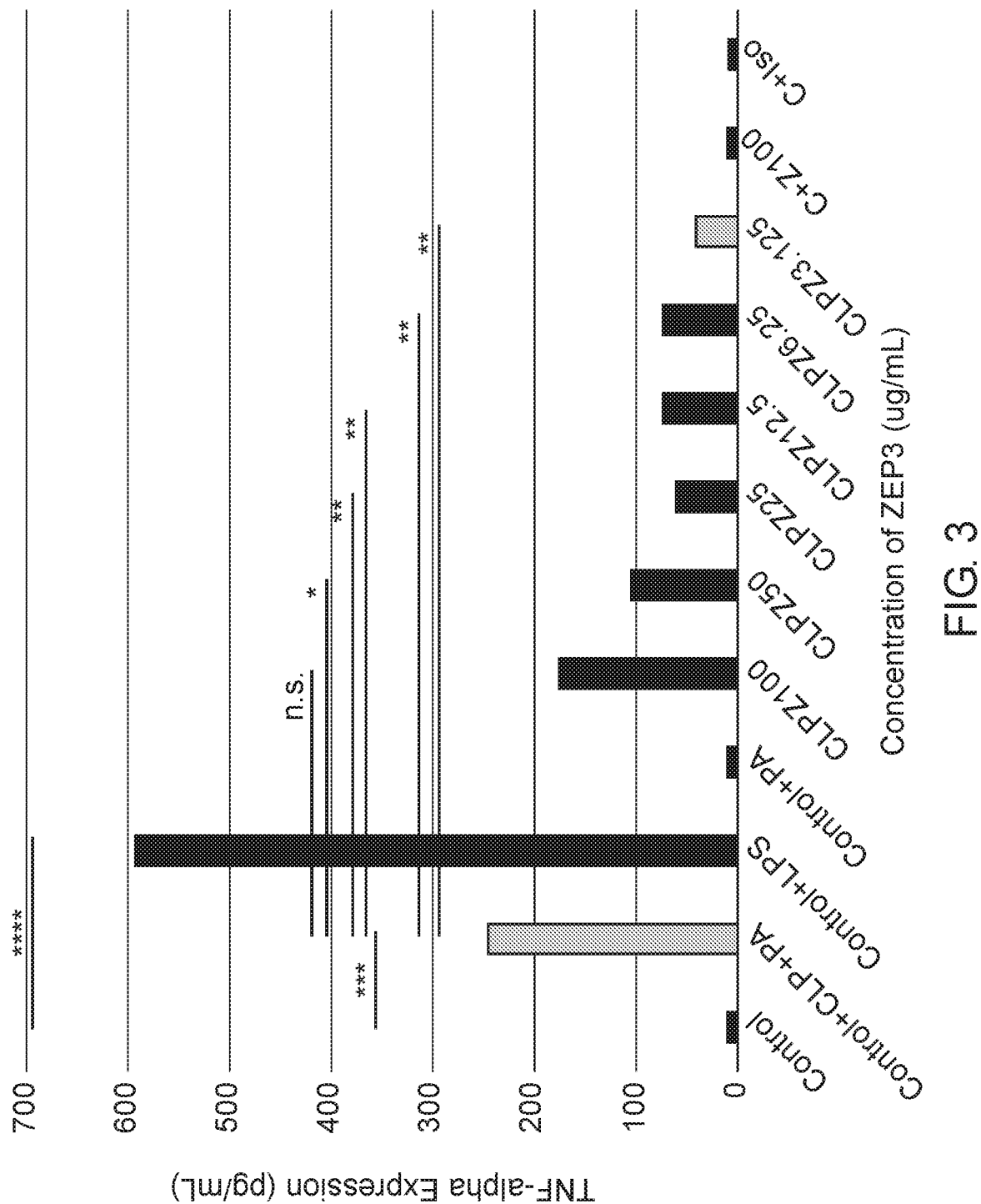
FIG. 3 is a bar graph illustrating the effect of ZEP3 (Z), (concentration range: 3.125-100 μg/ml) on the amount of TNFα produced by inflammation-induced macrophage cells. Lines marked by **, *, **, * and n.s. represent statistically significant difference at p<0.0001, p<0.001, p<0.01, P<0.1 and non-significant, respectively.

FIG. 3 and Table 3 below show that ZEP3 substantially reduced TNF alpha expression by macrophage cells treated with LPS and palmitic acid. The most effective concentration of ZEP3 under the experimental conditions was 3.125 µg/ml (82.90% reduction of TNF alpha expression; p<0.0001). ZEP3 $ED_{50}$ was estimated at 51.94 µg/mL.

TABLE 3

The effect of ZEP3 concentrations on the expression of TNF alpha by macrophages treated with LPS and Palmitic Acid

| Treatment | Mark | ZEP3 (µg/ml) | LPS (ng/mL) | palmitic acid (µM) | TNF alpha (pg/mL) | % reduction of TNF alpha |
|---|---|---|---|---|---|---|
| Cells control | Control | — | — | — | 11.022 | — |
| LPS and Palmitic acid control | Control + LPS + PA | — | 100 | 200 | 245.11 | — |
| LPS control | Control + LPS | — | 100 | — | 592.80 | — |
| Palmitic acid control | Control + PA | — | — | 200 | 11.21 | — |
| ZEP3-100 | CLPZ100 | 100 | 100 | 200 | 176.22 | 28.1 |
| ZEP3-50 | CLPZ50 | 50 | 100 | 200 | 106.75 | 56.4 |
| ZEP3-25 | CLPZ25 | 25 | 100 | 200 | 61.57 | 74.9 |
| ZEP3-12.5 | CLPZ12.5 | 12.5 | 100 | 200 | 74.83 | 69.5 |
| ZEP3-6.25 | CLPZ6.25 | 6.25 | 100 | 200 | 75.52 | 69.2 |
| ZEP3-3.125 | CLPZ3.125 | 3.125 | 100 | 200 | 41.98 | 82.9 |
| ZEP3 control | C + Z100 | 100 | — | — | 10.44 | — |
| Vehicle control (isopropanol) | C + Iso | — | — | — | 10.46 | — |

Example 4—the Effect of ZEP4 on the Expression of IL-1 Beta by Nigericin-Activated Macrophage Cells Materials and Methods The peptide ZEP4 (SEQ ID NO: 2), was synthesized as described hereinabove.

Expression of IL-1 Beta by Nigericin-Activated Macrophages.

Macrophage cells originating from C7BL/6 mice were cultured at a density of 200,000 cells/mL in a 24-well plate (500 µl wells) and incubated at 37° C. and 50 $CO_2$ overnight. Following the overnight incubation, media were replaced with fresh media containing 100 ng/mL LPS. Three hours later, the LPS-containing media were replaced with fresh media containing 50 µg/ml ZEP4 to treatment wells. Following one-hour incubation, Nigericin (20 mM) aliquots were added to the ZEP4 treated and LPS control wells. The plates were incubated for additional 24 hour and the amount of IL-1beta in each well was measured. Table 4 lists the different control and treatment groups. Reduction in TNF alpha production in the treatment group was calculated relative to cells treated with LPS and nigericin (LPS+N).

Results

Figure 4:
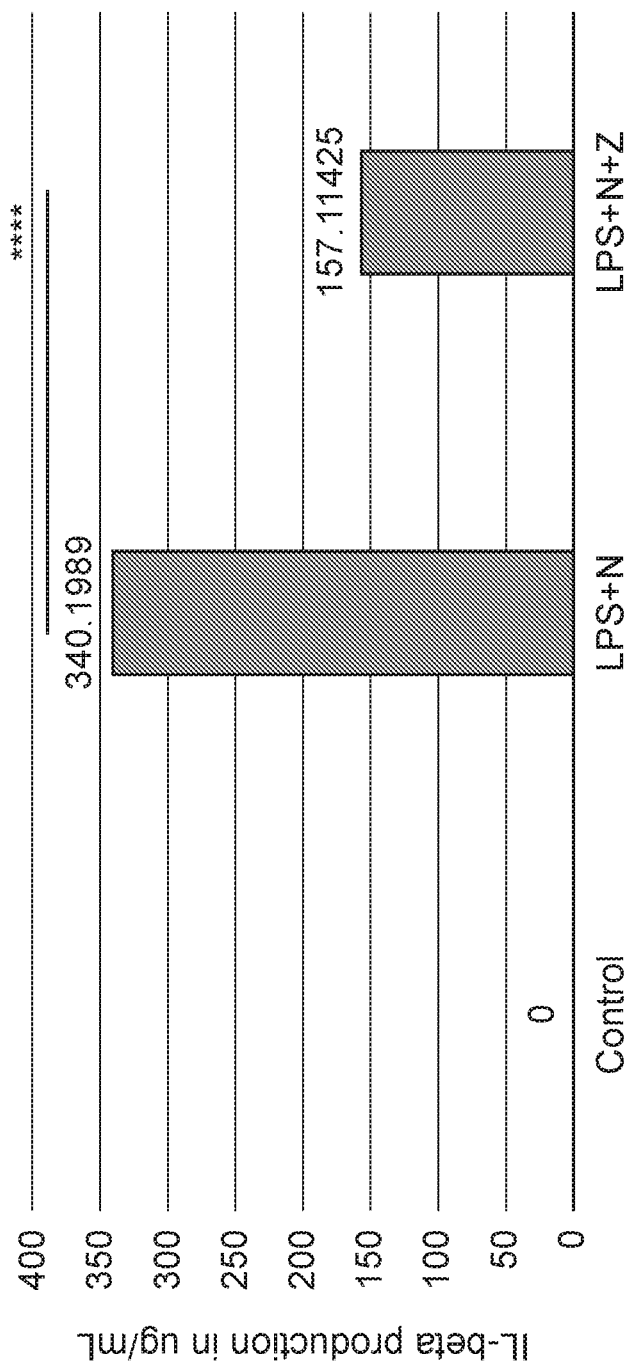
FIG. 4 is a bar graph illustrating the effect of ZEP4 (Z), (50 μg/ml) on the amount of IL-1beta produced by inflammation Nigericin-induced macrophage cells. Line marked by **** represents statistically significant difference at p<0.0001.

FIG. 4 and Table 4 below show that ZEP4 at a concentration of 50 µg/ml reduced the release of IL-1beta by Nigericin-activated macrophages by 53.8% (****p<0.0001).

TABLE 4

The effect of ZEP4 on the release of IL-1beta by Nigericin-activated macrophages

| Treatment | Mark | ZEP4 (μg/mL) | LPS (ng/mL) | Nigericin (mM) | IL-1beta (μg/mL) | % reduction of IL-1beta |
|---|---|---|---|---|---|---|
| Control | Control | — | — | — | — | — |
| LPS and nigericin control | LPS + N | — | 100 | 20 | 340.2 | — |
| ZEP4 | LPS + N + Z | 50 | 100 | 20 | 157.1 | 53.8**** |

Example 5—the Effect of ZEP3 on the Viability of Inflammation-Induced Macrophage Cells Materials and Methods The peptide ZEP3 (SEQ ID NO: 1), was synthesized as described in U.S. Pat. No. 7,220,725.

Effect of ZEP3 on the Viability of Macrophages Activated by LPS and Palmitic Acid Macrophages originating from C57BL/6 mice were cultured at a density of 200,000 cells/mL in a 24-well plate (500 μl well) and incubated at 37° C. and 5% $CO_2$ overnight. Following the overnight incubation, media were replaced with fresh media containing 100 ng/mL LPS, followed by three hours incubation. The LPS-containing media in the treatment groups were then replaced with fresh media containing ZEP3 at concentration of 50 μg/ml, followed by one-hour incubation. Next, palmitic acid (100, 200 or 400 μM) was added to the appropriate wells. The plates were incubated for additional 24 hours and the viability of cells was estimated using an LDH Cytotoxicity Assay Kit. Table 5 lists the different treatment and control groups.

Results

Figure 5:
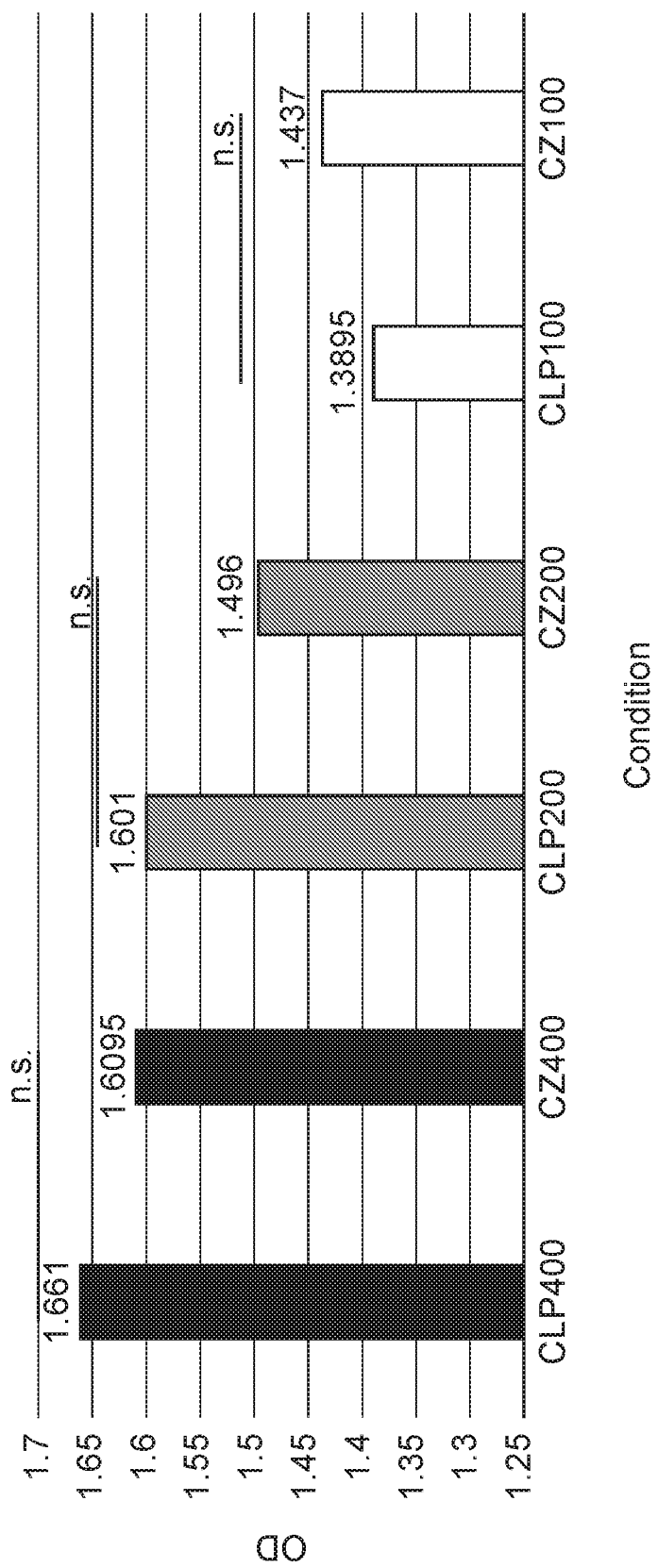
FIG. 5 is a bar graph illustrating the effect of ZEP3 on the viability of inflammation-induced macrophage cells.

FIG. 5 and Table 5 below show that ZEP3 had no significant effect on the viability of inflammation-induced macrophage cells under the experimental conditions.

TABLE 5

The effect of ZEP3 on the viability of B6 Macrophage cells activated with LPS and palmitic acid

| Treatment | ZEP3 (μg/ml) | LPS (ng/ml) | palmitic acid (μM) | OD | Statistical Significance |
|---|---|---|---|---|---|
| CLP400 | — | 100 | 400 | 1.661 | — |
| CZ400 | 50 | 100 | 400 | 1.6095 | n.s |
| CLP200 | — | 100 | 200 | 1.601 | — |
| CZ200 | 50 | 100 | 200 | 1.496 | n.s |
| CLP100 | — | 100 | 100 | 1.3895 | — |
| CZ100 | 50 | 100 | 100 | 1.437 | n.s |

Example 6—the Effect of ZEP3 Pretreatment on the Expression of TNF Alpha by Inflammation-Induced Macrophage Cells Materials and Methods The peptide ZEP3 (SEQ ID NO: 1), was synthesized as described in U.S. Pat. No. 7,220,725.

Expression of TNF Alpha by B6 Macrophage Cells

Macrophages originating from C57BL/6 mice were cultured at a density of 200,000 cells/mL in a 24-well plate (500 μl wells) and placed in a 37° C., 5% $CO_2$ Incubator overnight. Following the overnight incubation media were replaced with fresh media containing 50 μg/ml ZEP3. Following 1-hour incubation 100 ng/mL LPS was added to the appropriate wells, the plates were incubated for additional 24 hours, then the amount of TNF alpha in each well was measured.

Results

Table 6 below shows that pretreatment of macrophage cells with ZEP3 prior to the LPS induction resulted in 46.7% reduction in the TNF alpha produced by the cells (**$p<0.05$).

TABLE 6

The effect of ZEP3 pretreatment on the expression of TNF alpha by LPS treated macrophages

| Treatment | ZEP3 (μg/mL) | LPS (ng/mL) | TNF alpha (pg/mL) | % reduction of TNF alpha |
|---|---|---|---|---|
| Control | — | — | 0 | |
| LPS control | — | 100 | 189.884 | |
| ZEP3 | 50 | 100 | 101.15088 | 46.7** |

Example 7—Anti-Inflammatory Effects of ZEP3 in a Corneal Epithelial Cell Culture Dry Eye Disease Model The anti-inflammatory effect of the peptides in experimental corneal inflammation was tested in a cell culture model using various inflammasome inducers such as LPS, 4-HNE, Nigericin and others to model a dry-eye-disease (DED). Using a dose-response model, human primary corneal epithelial cells were pre-treated with the peptides followed by exposure to DED inducers. Expression of IL-6 was measured as well as cell viability, ROS production.

Materials and Methods

Human primary Corneal Epithelial Cells (PCS-700-010; HCECs) were treated with ZEP3 at concentrations ranging from 3 to 12 μg/ml for 2 hours then exposed to LPS, 4-HNE or Nigericin for 24 hours. Following incubation, the levels of the pro-inflammatory cytokine IL-6, cell viability and reactive oxygen species (ROS) production in the cell cultures were measured.

Results

Figure 7:
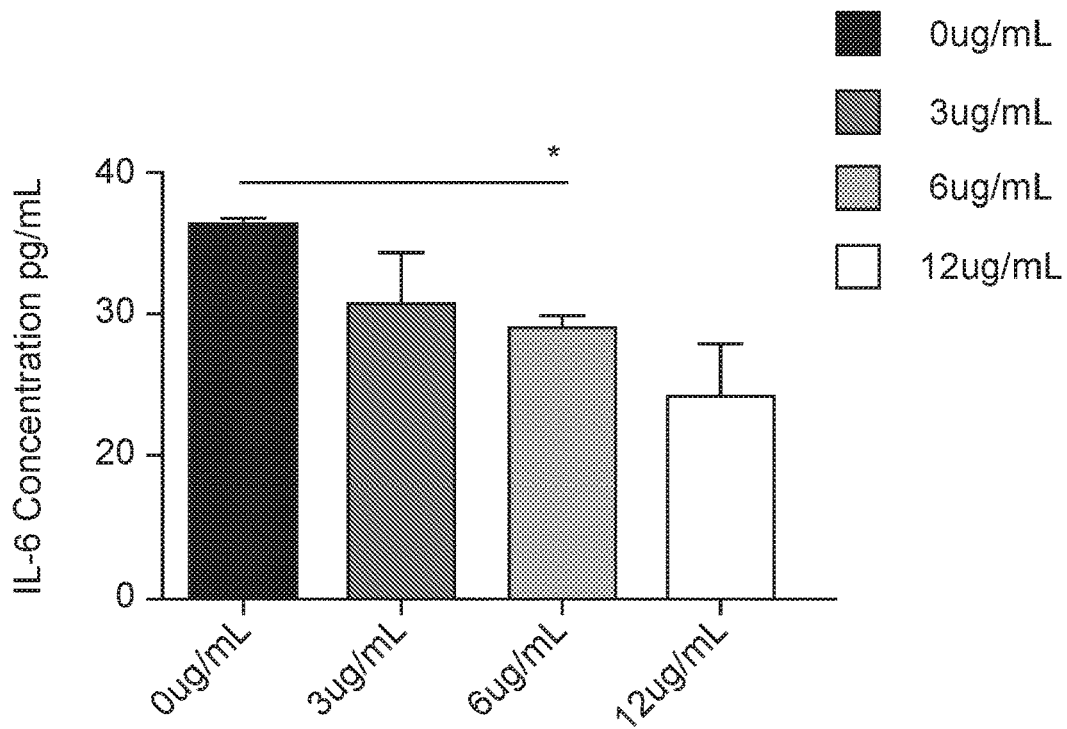
FIG. 7 is a bar graph illustrating the effect of ZEP3 at different concentrations on the amount of IL-6 produced by inflammation-induced corneal epithelial cells exposed to 4-Hydroxynonenal (4-HNE) for 24 hr. Line marked by * represents statistically significant difference at p<0.05.

As shown in FIG. 7 the level of IL-6 in cell culture decreased from 52.45±0.9121 μg/mL in the untreated cell culture, down to 38.08±1.368 μg/mL in the ZEP3 treated cells (27.4% reduction; $P<0.05$).

Figure 8:
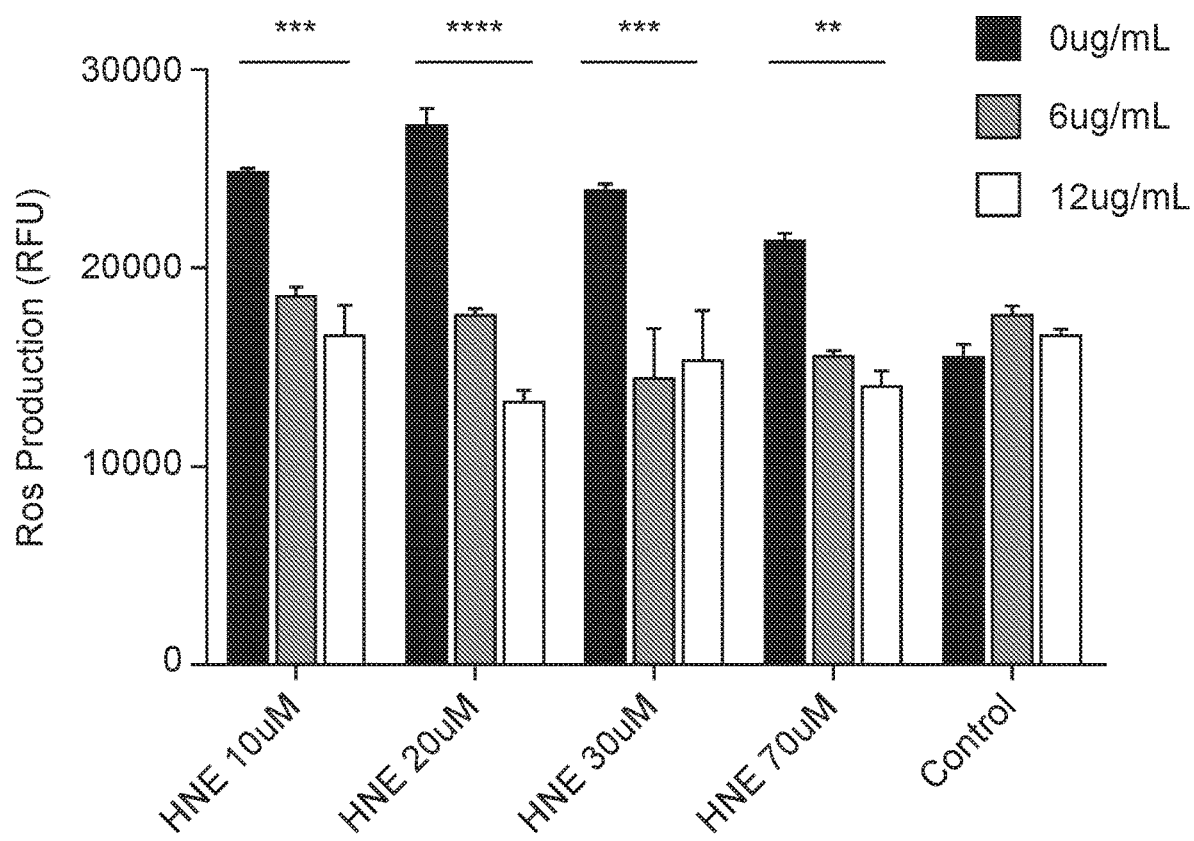
FIG. 8 is a bar graph illustrating the protective effect of ZEP3 at different concentrations on the amount of Reactive Oxygen Species (ROS, measured by DCFDA kit) produced by inflammation-induced corneal epithelial cells exposed to 4-HNE for 24 hours. Lines marked by **, * and ** represents statistically significant difference at p<0.0001, p<0.001 and p<0.01, respectively.
Figure 9:
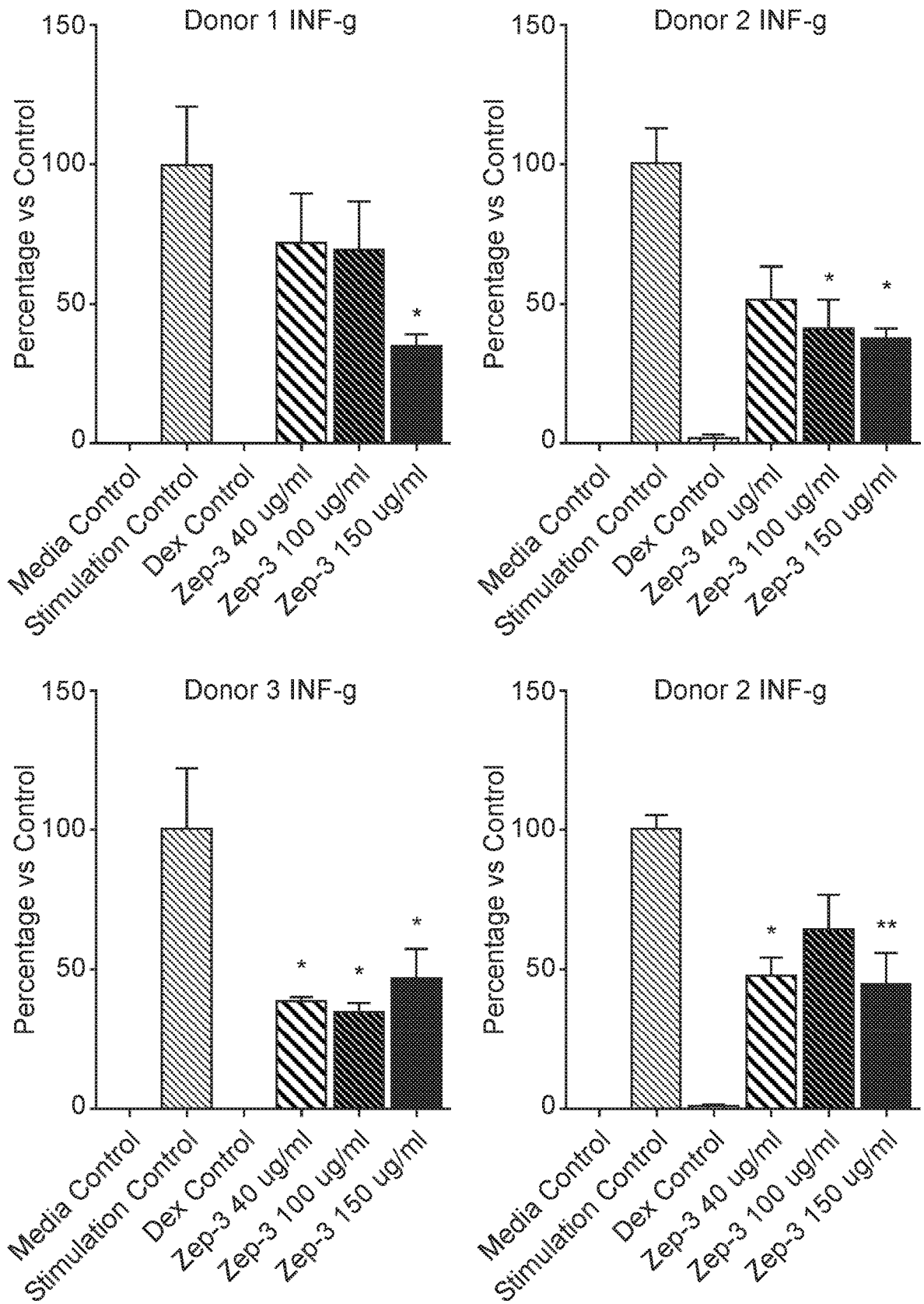
FIG. 9 describes IFN-γ production in normal PBMCs from 4 human donors, in response to stimulation with ZEP3 at different concentrations and media, stimulation and dexamethasone controls. Statistically significant differences are represented as: *p<0.05, **p<0.01, compared with stimulation control via 1-way ANOVA followed by Dunette's multiple comparisons.
Figure 10:
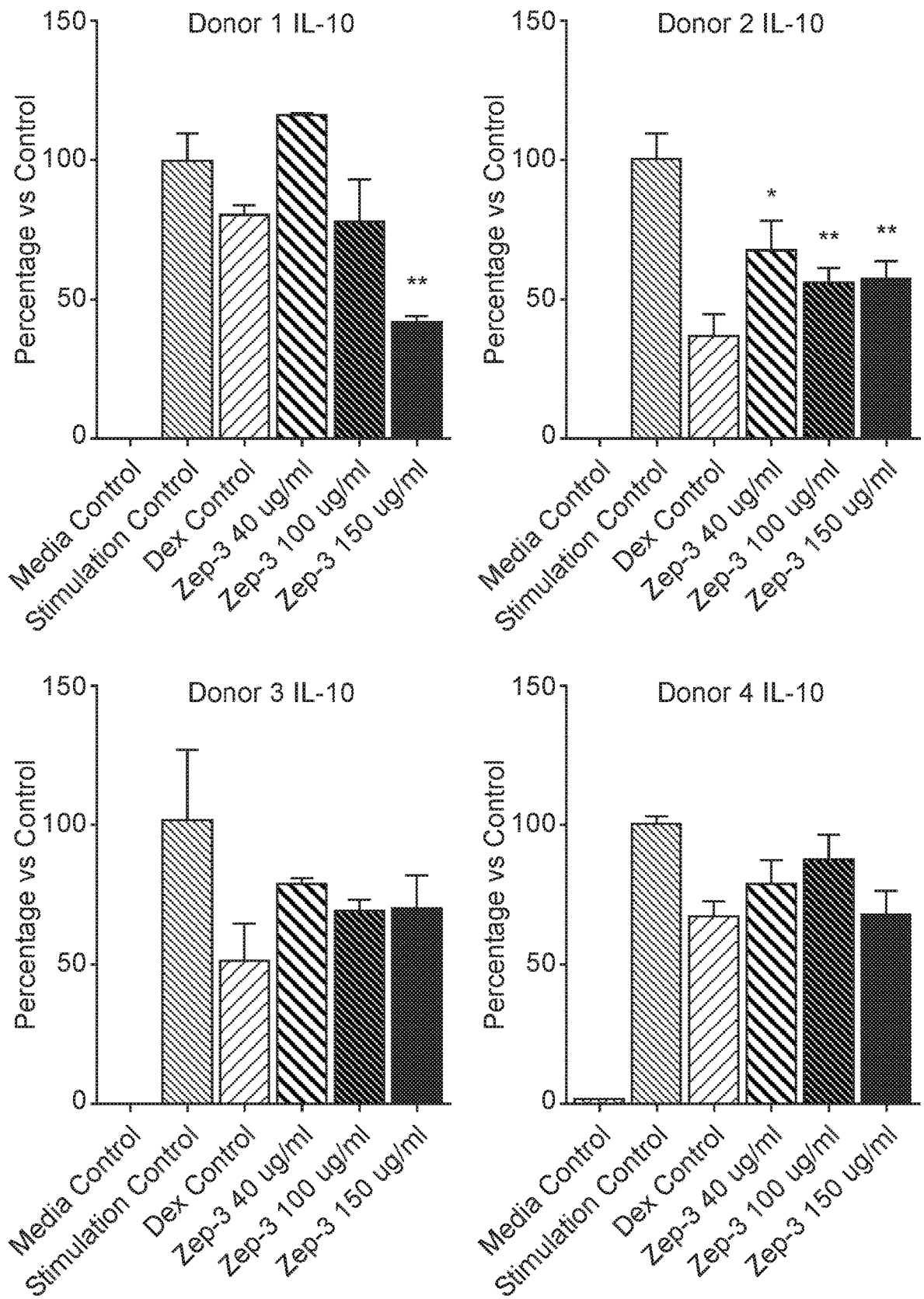
FIG. 10 describes production of IL-10 in normal PBMCs from four human donors, in response to stimulation with ZEP3 at different concentrations and media, stimulation and dexamethasone controls. Statistically significant differences are represented as: *p<0.05, **p<0.01, compared with stimulation control via 1-way ANOVA followed by Dunette's multiple comparisons.
Figure 11:
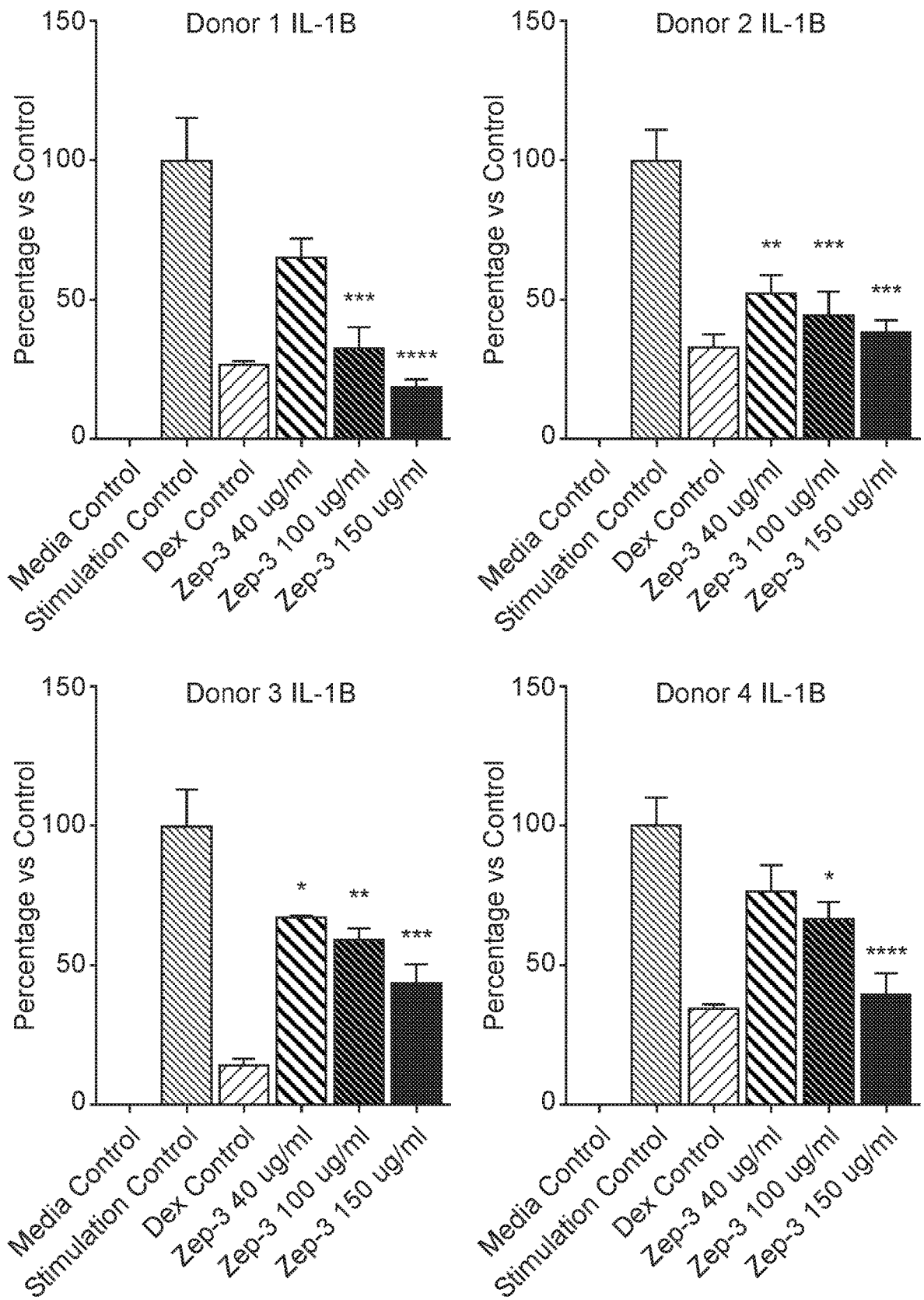
FIG. 11 depicts IL-1B production in normal PBMCs from 4 human donors, in response to stimulation with ZEP3 at different concentrations and media, stimulation and dexamethasone controls. Statistically significant differences are represented as: *p<0.05, p<0.01, *p<0.001, ****p<0.0001 compared with stimulation control via 1-way ANOVA followed by Dunette's multiple comparisons.
Figure 12:
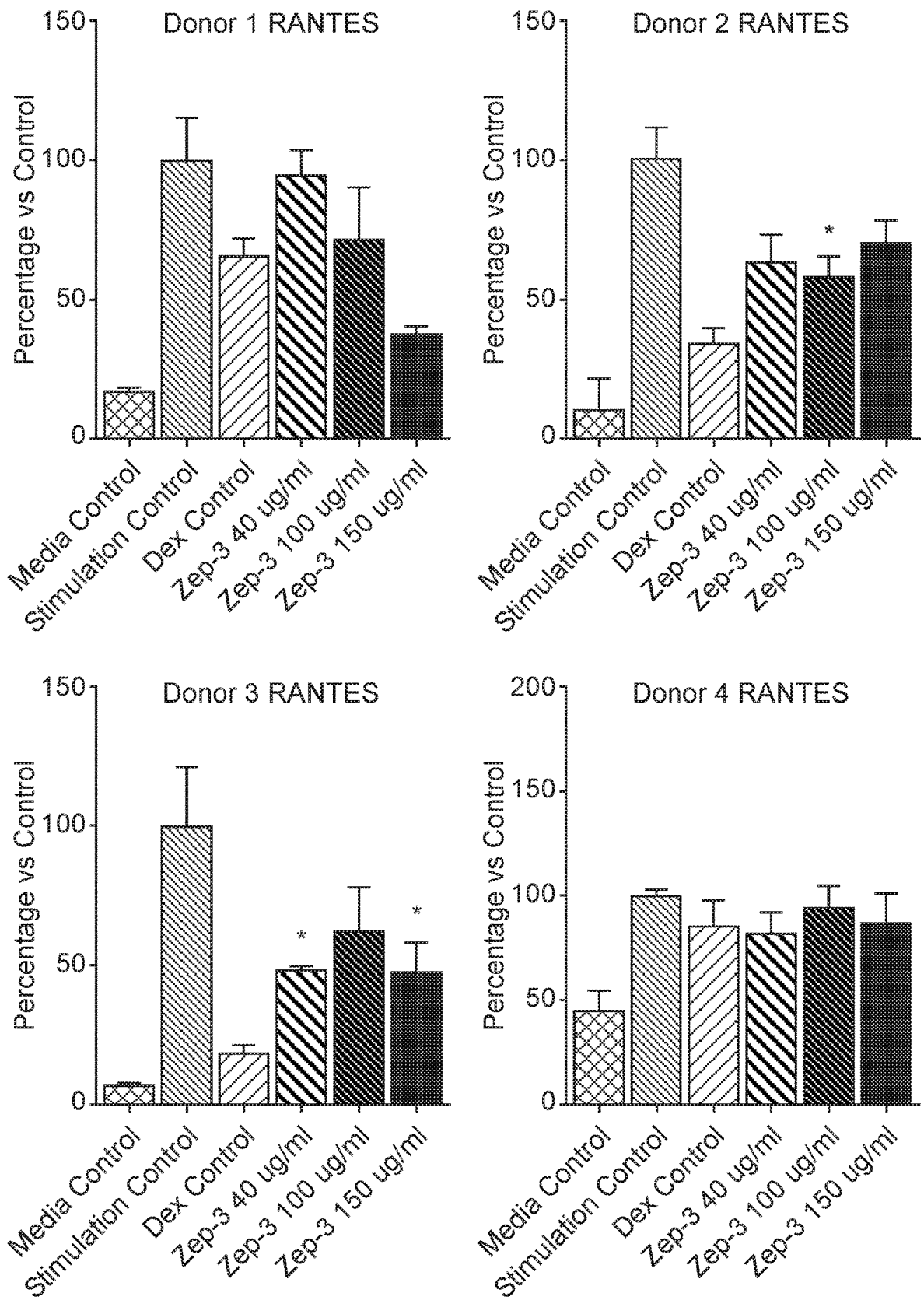
FIG. 12 represents RANTES production in normal PBMCs from 4 human donors, in response to stimulation with ZEP3 at different concentrations and media, stimulation and dexamethasone controls. Statistically significant differences are represented as: *p<0.05, compared with stimulation control via 1-way ANOVA followed by Dunette's multiple comparisons.

AS shown in FIG. 8 the level of ROS in cell culture (reported as relative fluorescence units; RFU) decreased from 27043±952 RFU in the untreated cell culture down to 13000±800 RFU in the cell culture treated with ZEP3 (51.9% reduction; $P<0.0001$).

Figure 6:
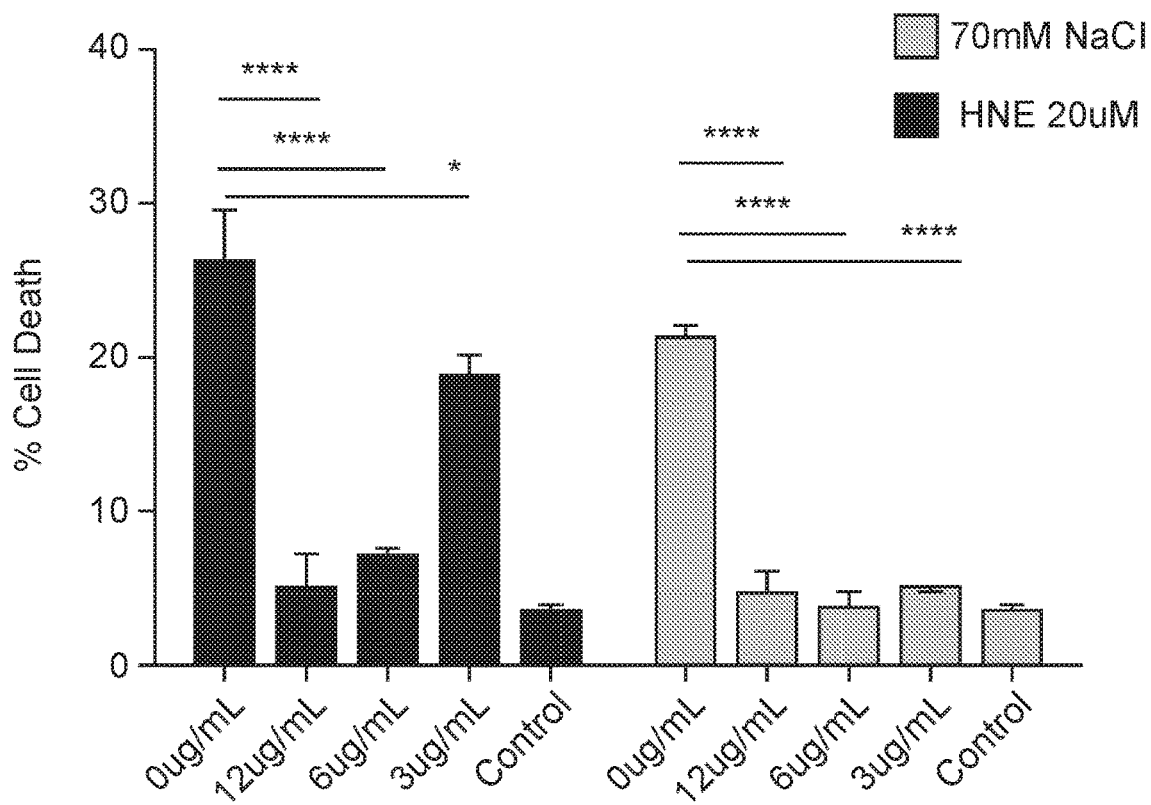
FIG. 6 is a bar graph illustrating the protective effect of ZEP3 at different concentrations on the viability of inflammation-induced corneal epithelial cells exposed to 70 mM NaCl (black bars) or to NHE20 (grey bars) determined via LDH assay. Lines marked by **** and * represent statistically significant difference at p<0.0001 and p<0.05, respectively.

As shown in FIG. 6 the cell death density decreased from 21.125±0.942% in the untreated cell culture down to 3.625±1.092% in cell the culture treated with ZEP3 (82.8% reduction; $P<0.0001$).

It is concluded that the ZEP3 peptide is effective in reducing corneal inflammation, restoring viability of HCECs and decreasing ROS production, factors that significant in DEA severity. The results provide a basis of use of this and similar peptides in preventing and treating DED caused by different pathologies.

Examples 1-7 hereinabove show that peptides ZEP3 (SEQ ID NO: 1) and ZEP4 (SEQ ID NO: 2), reduced the expression of the inflammatory cytokines TNF alpha, IL-1 beta and IL-6 in inflammation-induced macrophage and corneal epithelial cells. In addition, the peptides were capable of restoring viability of cells exposed to inflammation stress. The results indicate that the peptides of the invention are capable of effectively inhibiting or preventing inflammation in macrophage and corneal epithelial cells.

Example 8—the Effect of ZEP3, ZEP3 Sodium Salt and ZEP4 on Endotoxin-Induced Uveitis (EIU) in Rats The model is performed according to De Vos et al., Exp Eye Res 61: 667-675, 1995. EIU is induced in male Lewis rats, weighing 180 to 200 g by footpad injection of 200 μg of LPS that has been diluted in 0.1 mL of sterile water. Animals are then randomized in (4 peptides)×(three concentrations)=twelve groups. A non-treated induced group is used as control of induction.

Animals are examined with a slit lamp biomicroscope 24 hours later, corresponding to the peak severity for EIU. Clinical ocular inflammation is scored in each eye using a scale from 0 to 7 as follows: iris hyperemia and cell in the anterior chamber 0-2, (0=no sign; 1=mild; 2=severe) and flare, myosis and hypopion are scored 0 for no sign or 1 for presence. The maximum possible score is 7 (sum of the 5 parameter scores).

Example 9—the Effect of ZEP3, ZEP3 Sodium Salt and ZEP4 in a Controlled-Environment Chamber (CEC) Mouse Model of Dry Eye The model procedure is described in Barabino et al. (IOVS 46: 2766-2771, 2005). Briefly, 8 to 12-week old BALB/c mice are used in a controlled-environment chamber (CEC) where relative humidity (RH), temperature (T), and airflow (AF) are regulated and monitored. Mice are randomized and treated with ZEP3, ZEP sodium salt and ZEP4 (the test peptides). A non-treated induced group is used as control. The mice are then placed into the CEC and exposed to specific environmentally controlled conditions (RH=18.5% 5.1%, AF=15 L/min, T=21-23° C.) for 3, 7, 14, and 28 days. Control mice are kept in a normal environment (RH=50%-80%, no AF, T=21-23° C.) for the same duration. Aqueous tear production by means of the cotton thread test, corneal fluorescein staining (score, 0-15), and goblet cell density in the superior and inferior conjunctiva are measured by a masked observer.

Example 10—the Effect of ZEP3, ZEP3 Sodium Salt and ZEP4 in a Scopolamine Induced Rat Model of Dry Eye Male Sprague-Dawley rats weighing between 300 g and 350 g are used. Dry eye is induced using scopolamine (Sigma-Aldrich, St. Louis, Mo.), which is continuously and systemically delivered to the animals via an osmotic pump (2ML4 Alzet®; CedarLane, Burlington, Ontario) filled with scopolamine and implanted subcutaneously in the mid dorsal area between the scapulae. The wound is closed with 2-3 wound clips. After the surgery and again the next day, the animals are subcutaneously injected with Carprofen (0.5 mg/100 g) a non-steroidal anti-inflammatory drug and potent, long-acting analgesic in rodents. Animals are anaesthetized before the surgical pump implantation and before all endpoint testing in an Isofluorane 99.9% USP (Abraxis Bioscience, Richmond Hill, Ontario) chamber. Scopolamine is delivered at 12.5 mg/day and the data is evaluated at day 14.

The sterile solution of 0.175 g/mL of scopolamine hydrobromide (Sigma-Aldrich, St. Louis Mo.) is prepared in saline (0.9%) and filtered through a 0.22 um syringe-end filter (Millex-GC, Millipore Corp., Bedford, Mass.). The 2ML4 Alzet® pumps are filled with 2 mL of 0.175 g/mL scopolamine solution according to the manufacturer's instructions.

The groups of rat eyes tested are as follows: Group 1: Control rats (n=12 eyes from 6 rats). Group 2: Rats (n=12 eyes from 6 rats) are induced with dry eye by systemic administration of scopolamine continuously and the measurement of fluorescein staining was taken at day fourteen. Group 3: Rats (n=14 eyes from 7 rats) are induced with dry eye by systemic administration of scopolamine continuously and treated once topically on day eight with saline. Group 4: Rats (n=14 eyes from 7 rats) are induced with dry eye by systemic administration of scopolamine continuously and treated once topically on day eight with a test peptide.

Endpoints are: (i) reduction in corneal fluorescein staining as measured at day thirteen as compared to the saline-treated control; (ii) aqueous tear production and aqueous tear turnover as measured at day thirteen as compared to the untreated or scopolamine treated controls.

Example 11—the Effect of ZEP3, ZEP3 Sodium Salt and ZEP4 in a Rabbit Model of Keratoconjunctivitis Sicca Keratoconjunctivitis sicca (KCS) is created in the right eyes of 8 New Zealand white rabbits by surgically closing the lacrimal gland excretory duct, and removing the nictitating membrane, nictitans gland and harderian gland. All rabbits are left untreated for 8 weeks and KCS is confirmed by measuring elevated tear film osmolarity by taking 0.1-0.4 μL tear samples as described by J. Gilbard, et al. (Ophthalmol. 96: 677, 1978). A 3.0 mmol solution of UTP or analog is prepared in a preserved, isotonic buffer solution. Rabbits are randomized and treated with ZEP3, ZEP sodium salt and ZEP4 (the test peptides). An untreated group is used as control. After treatment began, 0.1-0.4 μL tear samples are taken from all rabbits for osmolarity measurements before the first dose. At 20 weeks the animals are sacrificed and goblet cell densities are measured by staining with alcian blue and periodic acid-Schiff's reagent (D. Dartt, et al., Exp. Eye Res. 67: 27, 1996).

Example 12—the Effect of ZEP3 and its Sodium Salt (ZEP3Na) on Cytokine Production in an In Vitro Model of Inflammation in Human PBMC The effect of the peptide ZEP3 (SEQ ID NO: 1) on cytokine production was evaluated in an in vitro human model of inflammation. Human Peripheral Blood Mononuclear Cells (PBMCs) were stimulated using Lipopolysaccharide (LPS) to produce cytokines.

Method: Briefly, cryopreserved human PBMCs of four healthy non-smokers, not on any corticosteroids or other inflammatory drugs, were grown in RPMI 1640 with 10% heat inactivated fetal bovine serum (FBS), 100 U/ml penicillin and 100 µg/mL streptomycin (complete growth medium, CGM).

Human PBMCs were thawed and plated for all groups (1-6, Table 7), and rested for 1 hour before treatment. Cell groups are treated with the teste item, ZEP3 (SEQ ID NO: 1) in concentrations of 40, 100 and 150 µg/ml, or dexamethasone, for 1 hour following by stimulation with LPS for 24 hours. Four hours before supernatant collection Almar Blue is added. 24 hours post LPS addition, Almar Blue fluorescent at 585 nm (correlating with cell viability), is measured and supernatant is collected for cytokine determination. Each group was tested in triplicate.

TABLE 7

The experimental groups used in the study

| Group | Stimulation (100 pg/ml) | Treatment | Treatment Timing |
|---|---|---|---|
| 1 | NA | NA (medium control) | NA |
| 2 | LPS | NA (stimulation control) | NA |
| 3 | LPS | 1 uM Dexamethasone | 1 hr pre-treatment |
| 4 | LPS | ZEP3 (40 µg/ml) | 1 hr pre-treatment |
| 5 | LPS | ZEP3 (100 µg/ml) | 1 hr pre-treatment |
| 6 | LPS | ZEP3 (150 µg/ml) | 1 hr pre-treatment |

Detailed method: cells were thawed according to manufacturer's instructions, washed in CGM and assessed for viability using trypan blue staining. A stock solution of 2×10^6 cells/mL was prepared in CGM. 100 µL of the stock solution were added to appropriate wells of a 96-well black-walled plate (one plate per donor), seeding 2×105 cells per well. Cells were incubated at 37° C. with 5% C02 for one hour. 100 µL of 2× test item, dexamethasone, or 1×CGM was added to the appropriate wells for a final volume of 200 µL/well. Plates were incubated a further 1 hour at 37° C. with 5% C02. After 1 hour, 20 µL of LPS was added to groups 2-9 to a final volume of 220 µL. 20 µL of IM were added to group 1. Cells were incubated at 37° C. with 5% C02 for 20 hours. At the 20-hour mark, 20 µL of Alamar Blue was added to all wells. Plates were incubated 37° C. with 5% C02 for a further 4 hours. At 24 hours post LPS stimulation, plates were read for assessment of cell viability and cell culture supernatants were harvested and stored at −80° C. for cytokine analysis. Remaining cells were washed 1× with sterile PBS. Cells were incubated in trypsin solution to detach from plate, spun to pellet, and trypsin solution was removed. Cells were then stored at −80° C. for optional further analysis. Luminex assay was used to determine the concentrations of GM-CSF, IFN-g, IL-10, IL-12p40, IL-17a, IL-10, IL-4, IL-6, RANTES, and TNF alpha present in supernatant samples collected after Alamar Blue assay. Manufacturer's protocols were followed in use of cytokine assay. Cytokine production and percentage of sample stimulation vs. the average of the stimulation control were calculated.

Results: As indicated in FIGS. 9-12, ZEP3 was shown to elicit a significant reduction of major mediators of inflammation including interferon gamma (IFNγ, FIG. 9), IL-10 (FIG. 10), IL-10 (FIG. 11) and RANTES (FIG. 12), supporting the notion of its anti-inflammatory effect. In some of the cytokines measured, a dose-dependent response was observed. No significant changes in viability of cells nor any trends in any donors were observed following treatment with the peptides in all concentrations tested indicating that the peptides are not cytotoxic to PBMCs. IL-4 and IL-17a levels were below the limit of detection in all tested groups.

The reduction in cytokine production was directly related to the ZEP3, confirming the anti-inflammatory effect of ZEP3 in human blood cells.

Example 13—In Vivo Atopic Dermatitis Model

The effect of topical administration of ZEP3 (SEQ ID NO: 1), and its sodium salt form (ZEP3Na), and ZEP4 (SEQ ID NO: 2) was evaluated in oxazolone-induced atopic dermatitis (AD) mouse models. This model is widely used and well described in literature (Avci et al. 2013 Expert Opin Drug Discov. 8, 331-355; Petersen T. K. 2006, Basic Clin. Pharmacol. Toxicol. 99, 104-115) as an accepted animal model for evaluating drugs for AD therapy in humans.

Method: Animals were sensitized by topical administration of oxazolone 2% in ethanol on the back at Day 0 after shaving and depilation of the animals (sensitization phase). Then a challenge was performed one week later by topical administration of oxazolone 1% in ethanol on the back and on right ear every 2 days at 10 occasions namely for total 3 weeks. The tested compounds were applied during the challenge phase every 2 days via the topical route as ready to use cream formulations. The surface of application was the same as for challenge (back+ear). 100 µL were deposited on the back and the back was smoothly massaged. Then, remaining formulation on finger glove was deposited on the internal face of the ear. Every other day, back skin and ears thickness were measured using caliper; and the following clinical scores were recorded from back skin: erythema and scaling. Animals were also weighed every other day (approximate bodyweights of a mouse at startup is about 20 g). Calibrated digital pictures of back skin zones were taken at Days 8, 18 & 28. At day 28 the experiment was terminated, animals were blood sampled and plasma specimens were separated. On euthanized animals, right ear and back skin samples were collected and frozen at −80° C. (sample from back skin and plasma) or kept in formalin (back skin and right ear samples) for further analysis. Table 8 describes the administration groups.

TABLE 8

The experimental groups tested in AD model

| Group | No. of animals | Compound | Conc. (mg/g)* | Dose (mg/kg) |
|---|---|---|---|---|
| 1/Control group | 8 | Excipient | 0 | 0 |
| 2/Reference group | 8 | Betamethasone (Diprosone ® 0.05%) | 0.5 | 2.5 |
| 3/Test group 1 | 8 | ZEP3 1% | 10 | 50 |
| 4/Test group 2 | 8 | ZEP3Na 1% | 10 | 50 |
| 5/Test group 3 | 8 | ZEP4 1% | 10 | 50 |

*In a volume of 100 µl for each animal.

The formulations used for topical administration of the tested compound were:

ZEP3 1% cream having pH 7.1 and comprising: Propylene glycol, Polysorbate 80, Edetate Disodium, Silicon dioxide (syloid), Methylparaben, White petrolatum, Isopropyl Myristate, Cetyl Alcohol and Glyceryl Monostearate.

ZEP3Na 1% cream having pH 8.0 and comprising: Propylene glycol, Polysorbate 80, Edetate Disodium, Silicon dioxide (syloid), Methylparaben, White petrolatum, Isopropyl Myristate, Cetyl Alcohol and Glyceryl Monostearate.

ZEP4 1% cream having pH 4.5 and comprising: Propylene glycol, Glycerin, Polysorbate 80, EDTA Disodium, Xanthan Gum, Silicon dioxide (syloid), Methylparaben, White petrolatum, Isopropyl Myristate, Cetyl Alcohol, Stearyl Alcohol, and Glyceryl Monostearate (kolliwax).

Results: Tested compounds ZEP3, ZEP3Na and ZEP4 administered at 50 mg/kg to atopic dermatitis induced mice were well tolerated. All peptides significantly reduced clinical lesions of atopic dermatitis, back skin thickness (FIGS. 13A and 13B), ear thickness (FIGS. 14A and 14B), and erythema (FIGS. 15A and 15B). Scaling was reduced from days 18 to 24 in mice treated with ZEP3 (FIG. 16A), and from days 14 to 24 in mice treated with ZEP3Na (FIG. 16A) or ZEP4 (FIG. 16B), indicating a delayed effect. Bodyweights of mice treated with ZEP3, ZEP3Na or ZEP4 behaved normally in comparison to the excipient (FIGS. 17A and 17B).

Figure 17A:
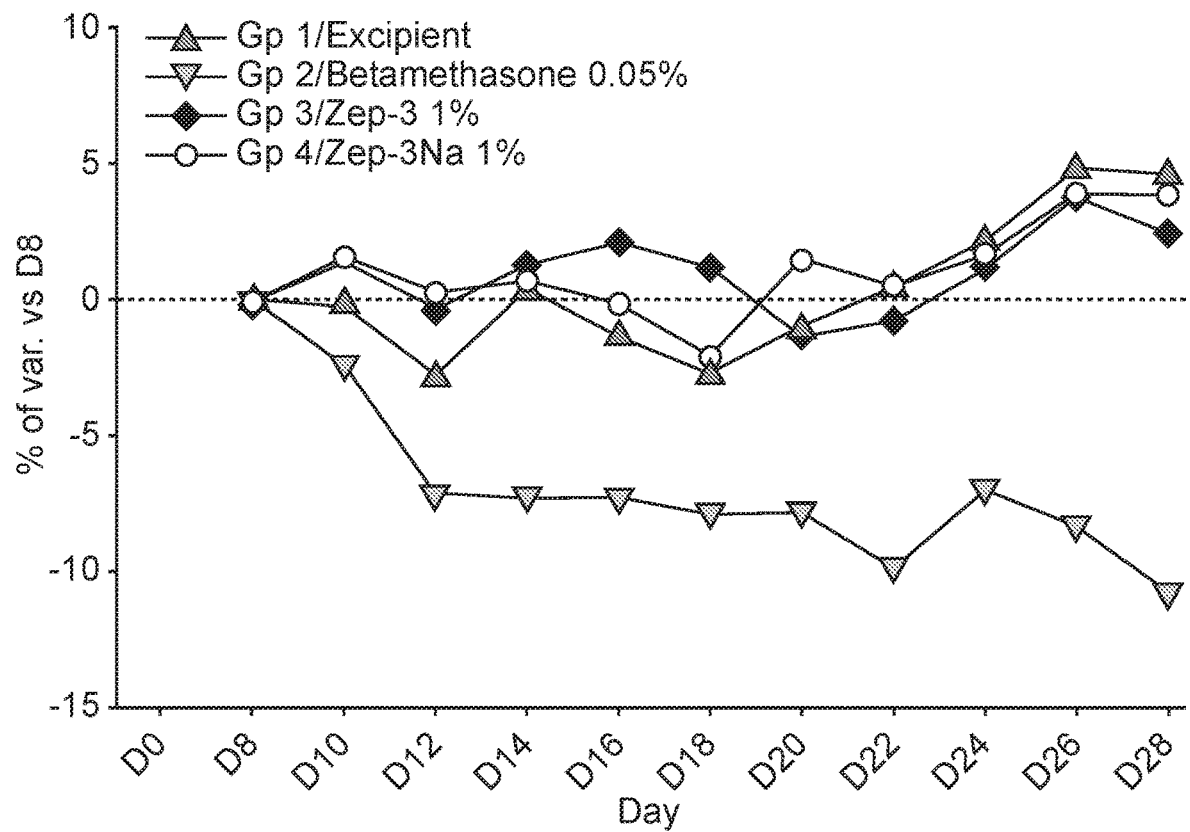
FIGS. 17A and 17B illustrate relative change of animal's bodyweights from day 8 to day 28, in mice treated topically with ZEP3, ZEP3Na (FIG. 17A) or ZEP4 (FIG. 17B), compared to excipient and betamethasone controls, in a mouse oxazolone-induced atopic dermatitis model.
Figure 17B:
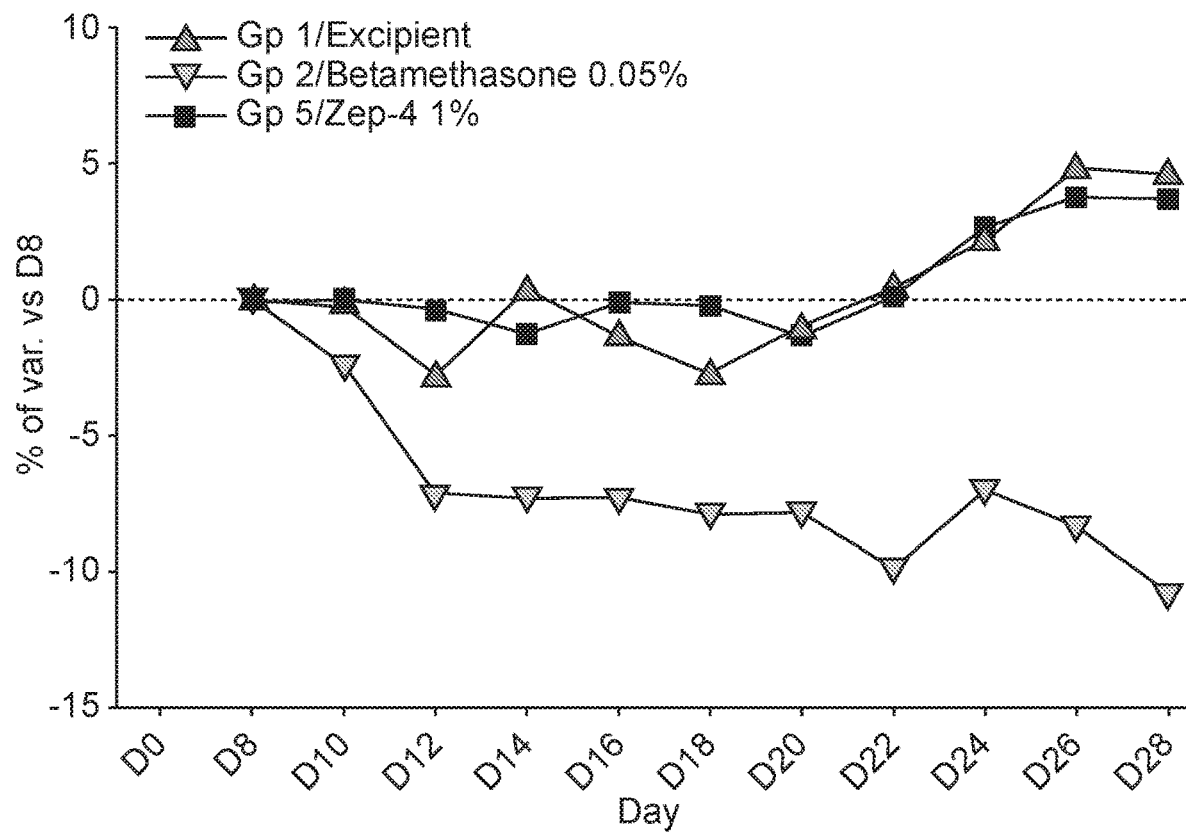

In details, Bodyweights for ZEP3, ZEP3Na and ZEP4 were quite stable during the first days of the study and showed an increase of about 3-4% at day 28 (FIGS. 17A and 17B). For the group treated with Betamethasone a bodyweight loss of about 8-10% was observed, as predicted.

Figure 13A:
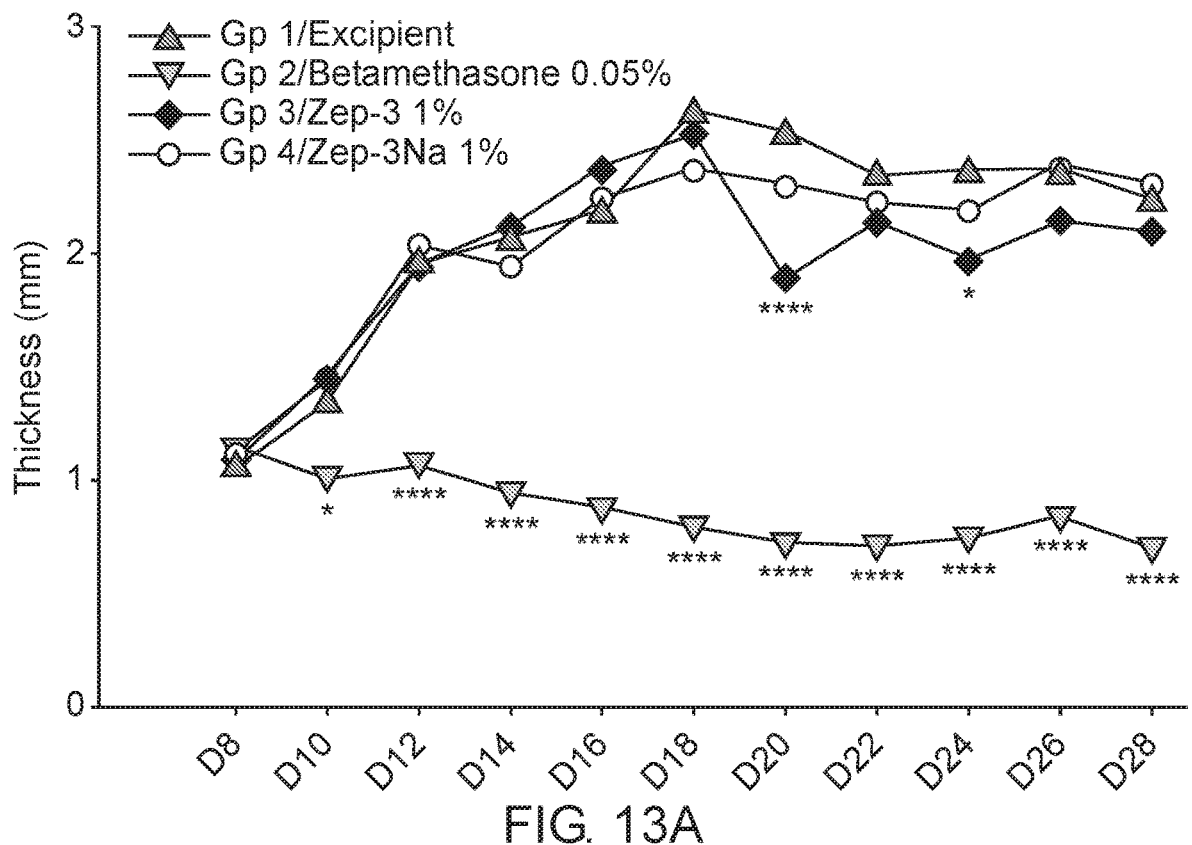
FIGS. 13A and 13B are graphs showing back skin thickness evolution over time, in mice treated topically with ZEP3, ZEP3Na (FIG. 13A) or ZEP4 (FIG. 13B), compared to excipient and betamethasone controls, in a mouse oxazolone-induced atopic dermatitis model. Statistically significant differences are represented as: *p<0.05, p<0.01, **p<0.001, compared with stimulation control via 1-way ANOVA followed by Dunette's multiple comparisons.
Figure 13B:
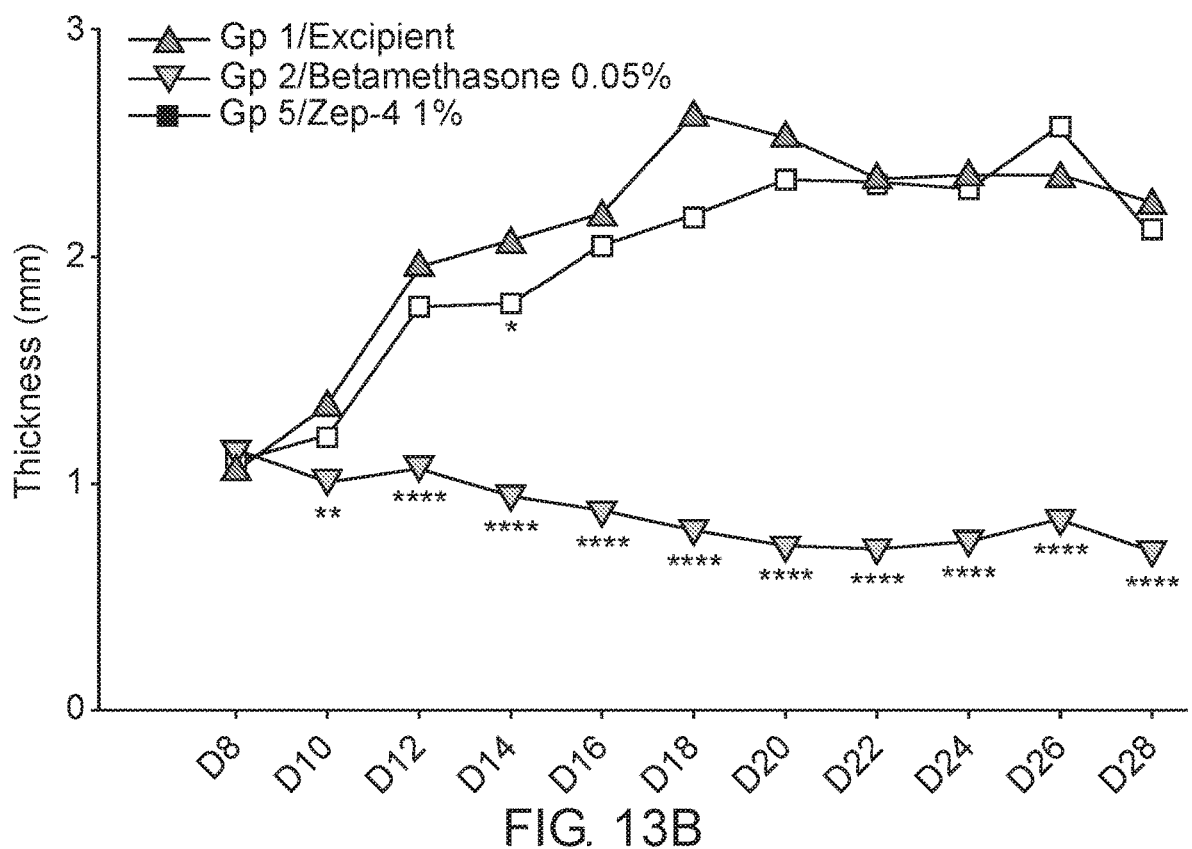

Back skin thickness increased during the first days of the study, except for the betamethasone treated mice, and then remained quite stable until the end of the study (FIGS. 13A and 13B). On day 28, an increase of around 110% was noticed for negative control Group administered with Excipient, 90% for Group 3 administered with ZEP3 1%, 105% for Group 4 administered with ZEP3Na 1% and around 90% for Group 5 administered with ZEP4 1%, whereas a decrease of 40% was noticed for positive control Group 2 administered with Betamethasone. All of the treated groups (groups 3, 4 and 5) presented graphically a trend to show back skin thickness lower than negative control Group 1. Significant difference on back thickness vs. control group 1 was outlined for ZEP3 at days 20 (−25.5%) and 24 (−16.6%). For ZEP4, Significant difference on back thickness vs. control group 1 was outlined at day 14 (−13.5%).

Figure 14A:
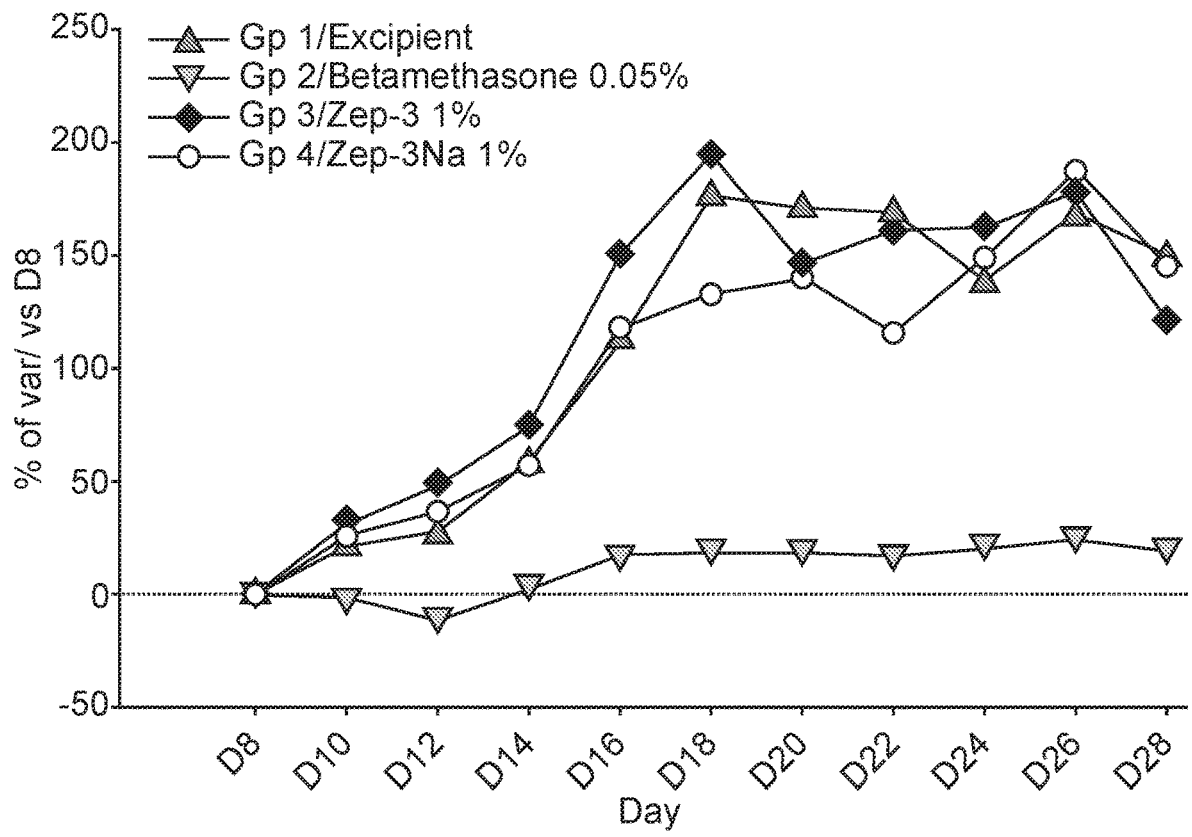
FIGS. 14A and 14B describe baseline-corrected right ear thickness evolution over time, in mice treated topically with ZEP3, ZEP3Na (FIG. 14A) or ZEP4 (FIG. 14B), compared to excipient and betamethasone controls, in a mouse oxazolone-induced atopic dermatitis model.
Figure 14B:
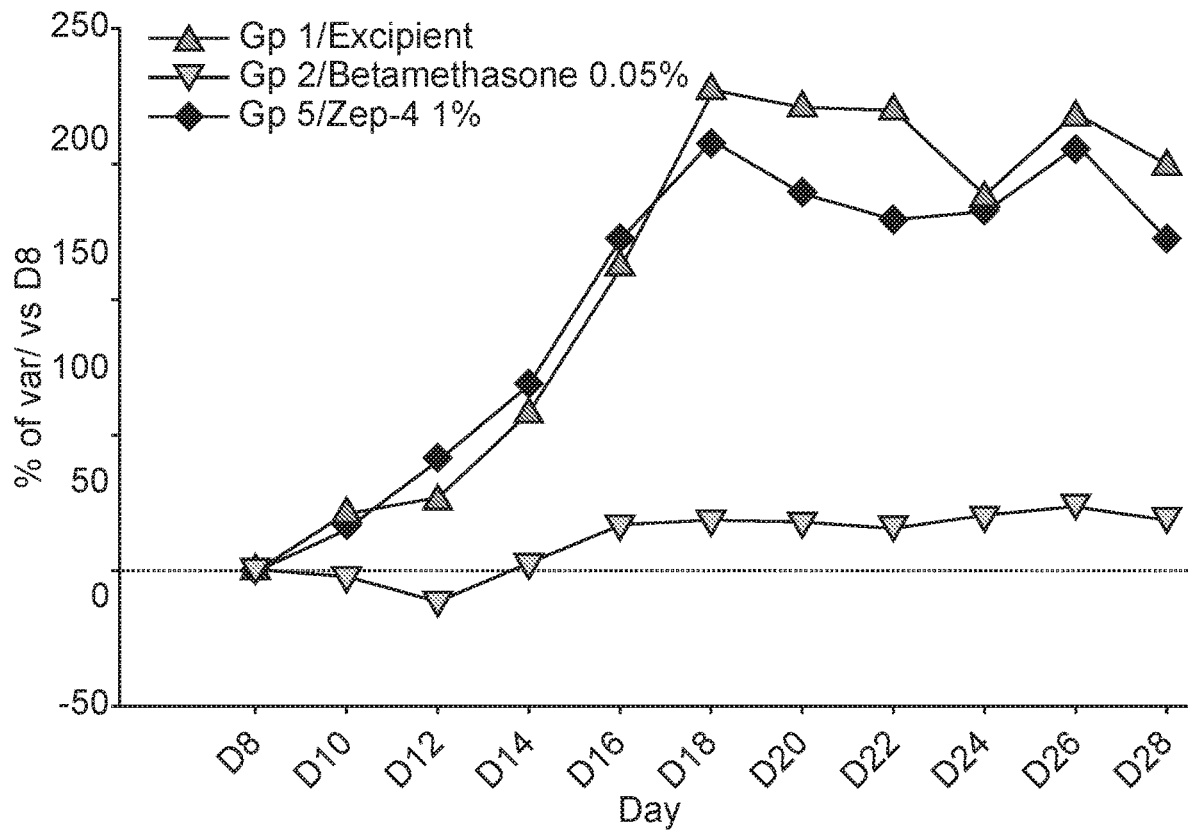
Figure 15A:
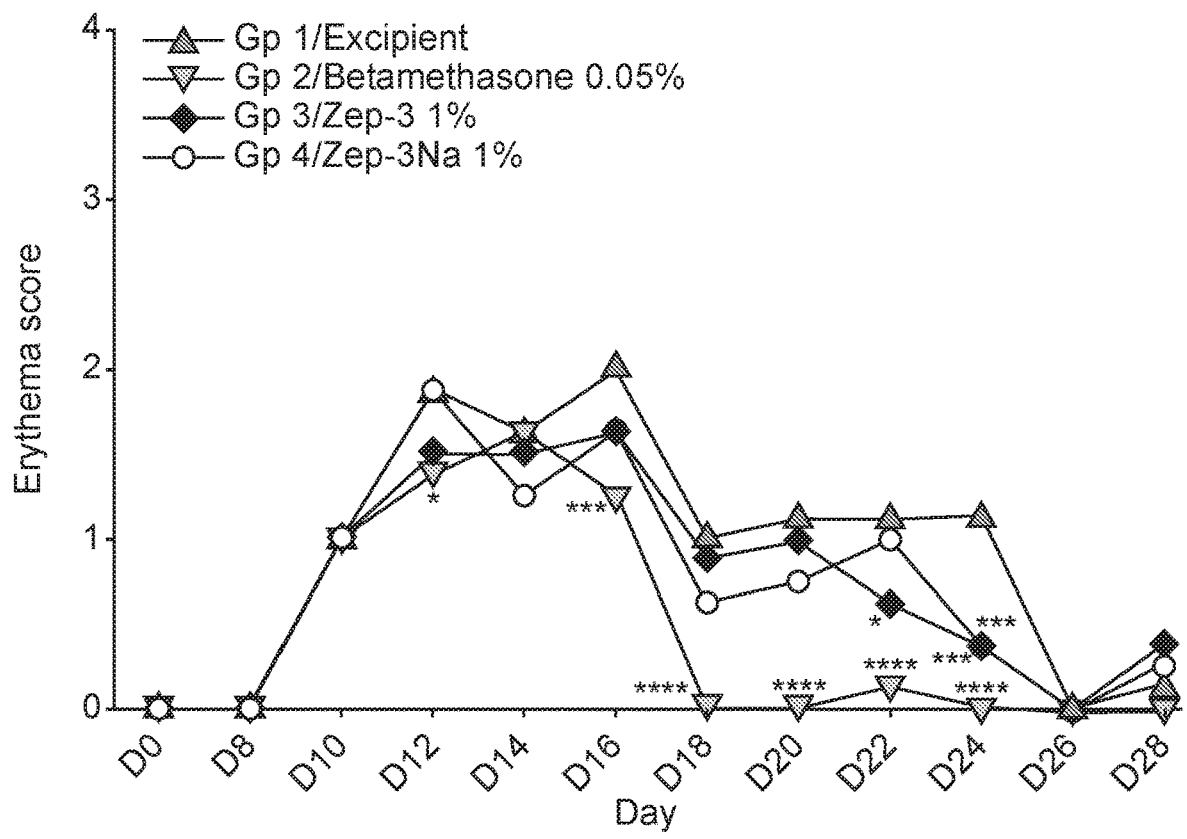
FIGS. 15A and 15B represent graphs displaying erythema score evolution over time in mice treated topically with ZEP3, ZEP3Na (FIG. 15A) or ZEP4 (FIG. 15B), compared to excipient and betamethasone controls, in a mouse oxazolone-induced atopic dermatitis model. Statistically significant differences are represented as: *p<0.05, p<0.001, **p<0.0001, compared with stimulation control via 1-way ANOVA followed by Dunette's multiple comparisons.
Figure 15B:
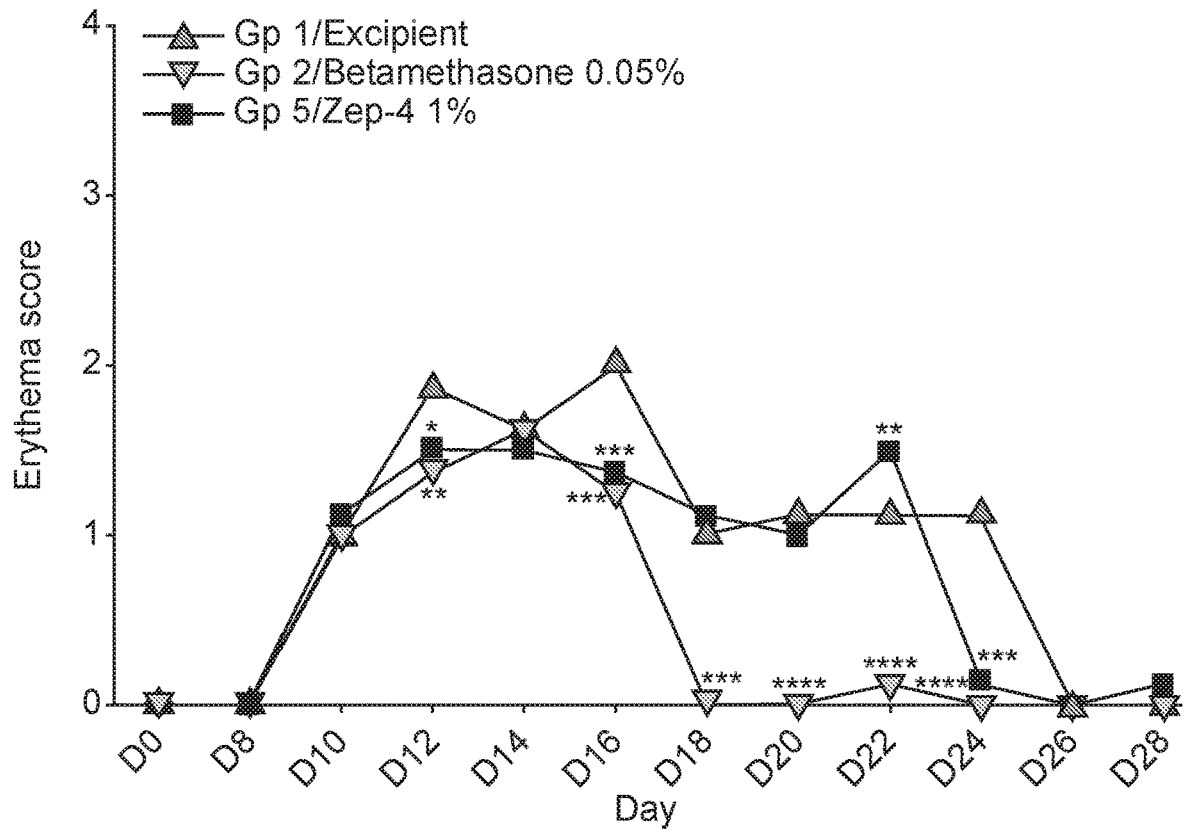

Right ear thickness: as observed typically with this model, all groups presented an important thickening from the first days until the end of the study, except positive control Group 2 which presented only a slight increase of about 15-20% during all the course of the study (FIGS. 14A and 14B). Significant difference was outlined at days 20, 22 and 28 for ZEP3 (−10.1 to −18.0% in comparison to control), at days 18, 20 and 22 for ZEP3 Na (−18.4 to −22.7% in comparison to control), and at days 20, 22, 28 for ZEP4 (−12.3 to −16.0% in comparison to control).

Erythema scoring was maximal on Day 16 for negative control Group (group 1) and then slightly decreased down to 0 on days 26-28. Erythema scoring recorded for test groups 3, 4 and 5 were similar to negative control group 1 (FIGS. 15A and 15B). A significant difference was shown at days 22 and 24 for ZEP3, at day 24 for ZEP3Na, and at days 12, 16, 22 and 24 for ZEP4.

Figure 16A:
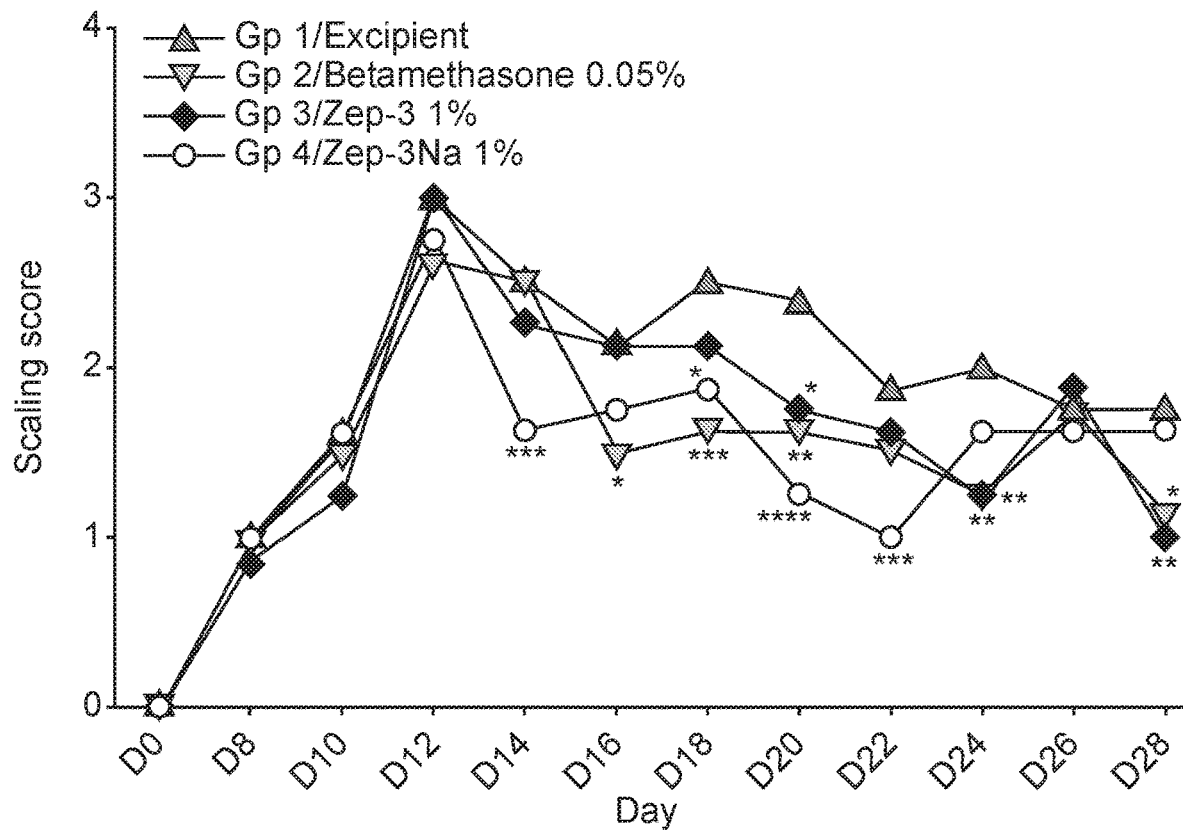
FIGS. 16A and 16B represent scaling score evolution over time in mice treated topically with ZEP3, ZEP3Na (FIG. 16A) or ZEP4 (FIG. 16B), compared to excipient and betamethasone controls, in a mouse oxazolone-induced atopic dermatitis model. Statistically significant differences are represented as: *p<0.05, p<0.01, *p<0.001, ****p<0.0001, compared with stimulation control via 1-way ANOVA followed by Dunette's multiple comparisons.
Figure 16B:
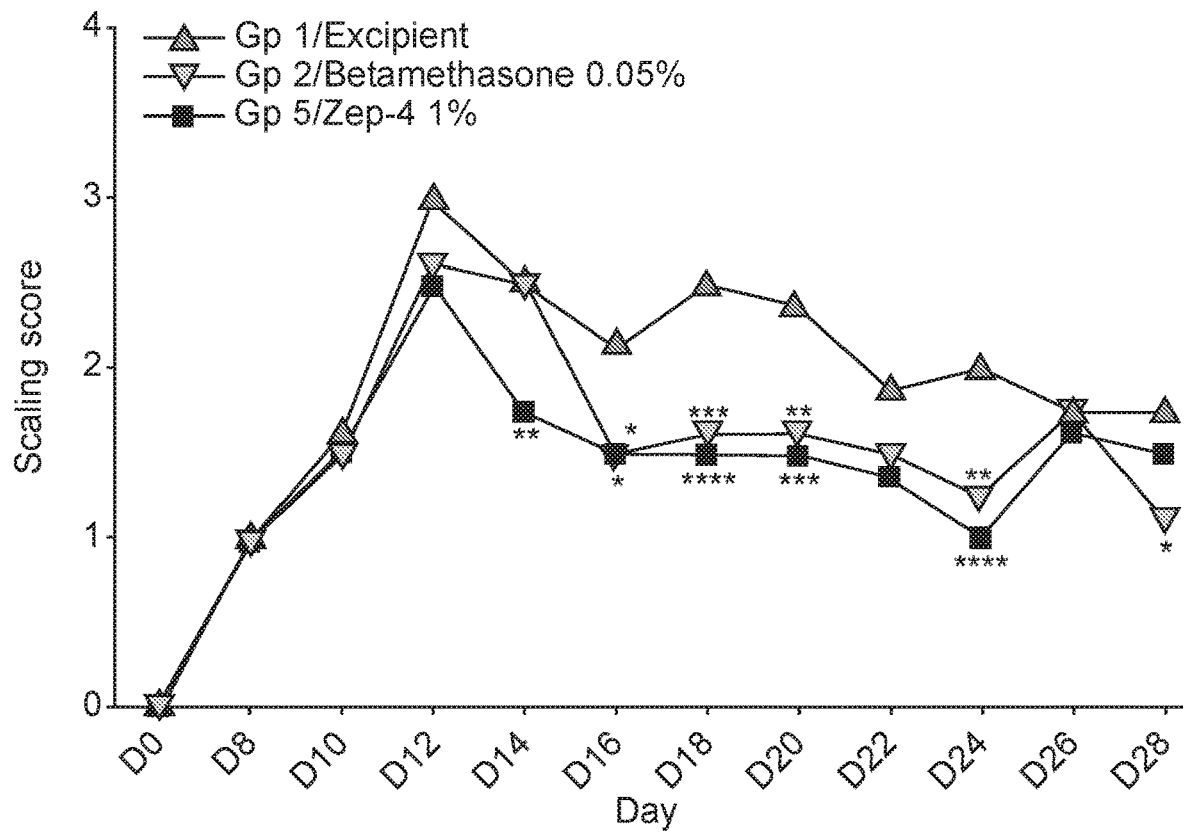

Scaling scoring progressively increased for the first days, then slightly decreased and remained quite stable for the second part of the study (FIGS. 16A and 16B). All treated groups 3, 4 and 5 presented a scaling score lower than negative control group 1 from day 14 to day 28.

Total scoring (sum of erythema and scaling scores) was also lower for treated groups 3, 4 and 5 than negative control group 1 from day 14 to day 28. Significant difference on total score was shown at days 20, 24 and 28 for ZEP3, at days 14, 18, 20 and 22 for ZEP3Na and at days 12-20, 24 and 28 for ZEP4.

Conclusion: The compounds ZEP3 and ZEP4 and their sodium salts, administered to atopic dermatitis induced mice at 50 mg/kg were well tolerated and significantly reduced clinical lesions of atopic dermatitis as shown by reduction of back skin thickness, ear thickness, erythema, and scaling.

Example 14. Treatment of Carpometacarpal Osteoarthritis (CMC Arthritis) with ZEP3

A male subject 75 years of age had an orthopedic surgeon diagnose him with CMC type arthritis of his big toe. His toe was swollen, red, and so painful that it prevented him from walking.

ZEP3 sodium salt at 0.5% cream was applied on the swollen area 5 times a day. The subject reported relief within one day of treatment and resolution of the condition within 3-4 days.

Example 15. The Effect of ZEP3 and ZEP3Na Peptides on TNF Alpha Secretion in Human Keratinocytes TNF alpha is a major pro-inflammatory mediator in keratinocytes. The compounds were tested for their anti-inflammatory effect by measuring their influence on TNF alpha levels.

Methods: SCCE020 cells (EpiGRO™ Human Epidermal Keratinocytes) were grown in complete growth medium (EpiGRO™ Human Keratinocytes Complete Medium; Millipore Cat. #SCMK001) for 4 passages. At passage 5, cells were seeded ($3*10^5$ cells/well) in triplicates in a volume of 1 ml complete growth medium per well. Additional 3 control wells contained only medium without cells. Upon adherence, cell medium was replaced by basal medium containing L-Glutamine without supplements (starvation medium) and cells were starved overnight. The next day, 24 hours after seeding, the cells were treated with ZEP3 or ZEP3Na or appropriate diluent (PBS or DMSO). After 4 hours of incubation, LPS (from E. Coli 055: B5; Sigma Cat. #L6529-1MG) was added to the wells in final concentration of 20 or 30 µg/ml. The experimental groups (three wells for each treatment) are summarized in Table 9.

Cells were incubated for 24 hours in tissue culture incubator. After collecting cell supernatants from all wells, cells from treatment groups: 1, 2, 3, 8, 9, 10, 13, 14 (without DMSO groups) were pelleted and stored at −80° C. for further analyses. The cells were collected from as following: upon supernatants collection, the wells were rinsed with trypsin, then incubated with trypsin until they detached from the plate surface, centrifuged, washed with PBS and stored as a cell pellet. TNF-α concentration in the supernatants was measured by ELISA (Quantikine HS ELISA; R&D Systems Cat. #HSTA00D), in 5 replicates.

Results: ZEP3 and ZEP4 effectively diminished TN alpha levels in human keratinocytes cell culture. TNF alpha concentration in the samples was calculated according to the standard curve trend line equation: =0.063x+0.1718. Percent inhibition of TNF alpha production was calculated in each treatment group in comparison to the corresponding control group (same conditions, without peptide). The results are summarized in Table 9.

TABLE 9

Experimental conditions, results and analysis

| # | DMSO | Peptide (mg/ml) | LPS (μg/ml) | TNFα (pg/ml) | St. Dev | Fold Change* | % Inhibition | t-Test** | t-Test Array 2 |
|---|---|---|---|---|---|---|---|---|---|
| 1[&] | — | — | — | 0 | 0 | — | | | |
| 2 | — | — | — | 2.8 | 0.3 | 1.0 | — | | 1 |
| 3 | — | — | 20 | 12.4 | 0.6 | 4.4 | — | $7.4 \times 10^{-8}$ | 2 |
| 4 | 0.10% | — | 20 | 8.8 | 0.7 | 3.1 | — | $1.7 \times 10^{-5}$ | 3 |
| 5 | 0.10% | ZEP3 0.4 | 20 | 4.6 | 0.5 | 1.6 | 48 | $5.1 \times 10^{-6}$ | 4 |
| 6 | 0.05% | ZEP3 0.2 | 20 | 6.0 | 0.4 | 2.1 | 32 | $7.1 \times 10^{-4}$ | 4 |
| 7 | 0.025% | ZEP3 0.02 | 20 | 9.6 | 0.5 | 3.4 | — | — | — |
| 8 | — | ZEP3Na 0.4 | 20 | 5.9 | 0.5 | 2.1 | 52 | $8.6 \times 10^{-8}$ | 3 |
| 9 | — | ZEP3Na 0.2 | 20 | 6.7 | 1.0 | 2.4 | 46 | $1.5 \times 10^{-5}$ | 3 |
| 10 | — | ZEP3Na 0.02 | 20 | 9.2 | 0.7 | 3.3 | 26 | $7.8 \times 10^{-5}$ | 3 |
| 11 | 0.10% | — | 30 | 21.5 | 2.2 | 7.6 | — | 0.75 | 13 |
| 12 | 0.10% | ZEP3 0.2 | 30 | 17.3 | 1.2 | 6.1 | 20 | 0.009 | 11 |
| 13 | — | — | 30 | 21.0 | 1.8 | 7.5 | — | $1.4 \times 10^{-5}$ | 2 |
| 14 | — | ZEP3Na 0.2 | 30 | 13.1 | 0.8 | 4.7 | 38 | $1.5 \times 10^{-4}$ | 13 |

[&]No cells
*Fold change of each sample refers to TNF-α concentration in sample #2.
**t-Test was performed using Microsoft EXCEL function for each sample (Array 1) versus the control of that sample (Array 2).
Parameters used for the t-Test: two-tailed distribution, unpaired t-Test, unequal variance. Same control reference sample was used for the calculation of percent inhibition of TNF-α secretion.

Conclusions: Quantitative test by ELISA has demonstrated dose dependent inhibition of TNF-α production in LPS treated human keratinocytes with either ZEP3 or ZEP3Na compared with the amount secreted by cells simulated with LPS alone.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

The invention claimed is:

1. A method of reducing the release or inhibiting the activity of at least one inflammatory or pro-inflammatory mediator, the method comprising administering to a subject in need thereof a pharmaceutical composition comprising a therapeutically effective amount of a tetrapeptide selected from the group consisting of pGlu-Asn-Trp-Lys-OH (SEQ ID NO: 3) and pGlu-Asn-Trp-Thr-OH (SEQ ID NO: 2), or a pharmaceutically acceptable salt or derivative thereof, wherein the derivative is selected from the group consisting of aliphatic ester of the carboxyl group, amide of the carboxyl group, N-acyl derivatives of free amino group, and O-acyl derivative of free hydroxyl group, and wherein the subject has an inflammatory disease or disorder selected from the group consisting of an eye inflammatory disease or disorder, an ear inflammatory disease or disorder, a lung inflammatory disease or disorder, a bowel inflammatory disease or disorder, and an inflammatory autoimmune disease or disorder.

2. The method of claim 1, wherein the at least one inflammatory or pro-inflammatory mediator is an inflammatory cytokine selected from the group consisting of: interferon gamma (IFN gamma), interleukin 1 beta (IL-1 beta), interleukin 10 (IL-10), tumor necrosis factor alpha (TNF alpha), and interleukin 6 (IL-6).

3. The method of claim 1, wherein the at least one inflammatory or pro-inflammatory mediator is an inflammatory mediator or chemokine selected from the group consisting of reactive oxygen species (ROS) and regulated upon activation normal T cell expressed and presumably secreted (RANTES).

4. The method of claim 1, wherein the tetrapeptide derivative comprises a C4 to C30 alkyl group attached to an amino group of a side chain or a terminal amine of the tetrapeptide.

5. The method of claim 4, wherein the alkyl group is attached by an amide linkage.

6. The method of claim 1, wherein the tetrapeptide consists of a sequence selected from the group consisting of pGlu-Asn-Trp-Lys(Octanoyl)-OH (SEQ ID NO: 1), pGlu-Asn-Trp-Thr-OH (SEQ ID NO: 2), or a pharmaceutically acceptable salt or derivative thereof.

7. The method of claim 6, wherein the pharmaceutically acceptable salt is a sodium salt of the tetrapeptide.

8. The method of claim 1, wherein the administration to the subject in need thereof is via a route selected from the group consisting of topical, ophthalmic, oral, nasal, and parenteral administration.

9. The method of claim 1, wherein the pharmaceutically acceptable salt is a sodium salt of the tetrapeptide.

10. The method of claim 1, wherein the eye inflammatory disease or disorder is selected from the group consisting of uveitis, dry eye syndrome, inflammatory symptoms associated with an infectious eye disease, an allergic eye disease, keratitis, conjunctivitis, meibomian gland dysfunction, and ocular symptoms associated with Sjogren syndrome.

11. The method of claim 1, wherein the subject has the eye inflammatory disease or disorder, and wherein the pharmaceutical composition is formulated in a form selected from the group consisting of a liquid solution or suspension for use as eyedrops, an emulsion, a cream, an ointment, a spray, a gel, and an intravitreal injection.

12. The method of claim 1, wherein the inflammatory autoimmune disease or disorder is selected from the group consisting of rheumatoid arthritis, osteoarthritis, psoriatic arthritis, ankylosing spondylitis, juvenile idiopathic arthritis, Sjogren syndrome, and lupus.

13. The method of claim 1, wherein the bowel inflammatory disease or disorder is selected from the group consisting of Crohn's disease and ulcerative colitis.

14. The method of claim 1, wherein the lung inflammatory disease or disorder is selected from the group consisting of asthma, bronchitis, pleurisy, alveolitis, vasculitis, pneumonia, chronic bronchitis, bronchiectasis, diffuse panbronchiolitis, hypersensitivity pneumonitis, idiopathic pulmonary fibrosis, and cystic fibrosis.

15. The method of claim 1, wherein the ear inflammatory disease or disorder is selected from the group consisting of inflammatory symptoms associated with ear infection, otitis media, otitis externa, mastoiditis, and otomastoiditis.

* * * * *

SEQUENCE LISTING

```
<160> NUMBER OF SEQ ID NOS: 3

<210> SEQ ID NO 1
<211> LENGTH: 4
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: pyroglutamic acid (pGlu)
<220> FEATURE:
<221> NAME/KEY: MOD_RES
<222> LOCATION: (4)..(4)
<223> OTHER INFORMATION: C8 alkyl attached to the epsilon amine of the
      Lysine side chain to form Lys(Octanoyl)

<400> SEQUENCE: 1

Glu Asn Trp Lys
1

<210> SEQ ID NO 2
<211> LENGTH: 4
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
```

```
<223> OTHER INFORMATION: pyroglutamic acid (pGlu)

<400> SEQUENCE: 2

Glu Asn Trp Thr
1

<210> SEQ ID NO 3
<211> LENGTH: 4
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: pyroglutamic acid (pGlu)

<400> SEQUENCE: 3

Glu Asn Trp Lys
1
```